(12) United States Patent
Schorey et al.

(10) Patent No.: US 11,284,844 B2
(45) Date of Patent: Mar. 29, 2022

(54) ELECTROMYOGRAPHY (EMG) ASSISTIVE COMMUNICATIONS DEVICE WITH CONTEXT-SENSITIVE USER INTERFACE

(71) Applicant: Control Bionics Holdings Pty Ltd., Sydney (AU)

(72) Inventors: James E. Schorey, Milford, OH (US); Peter S. Ford, Sydney (AU); Robert W. Wong, Sydney (AU)

(73) Assignee: Control Bionics Holdings Pty Ltd., Sydney (AU)

( * ) Notice: Subject to any disclaimer, the term of this patent is extended or adjusted under 35 U.S.C. 154(b) by 77 days.

(21) Appl. No.: 16/192,976

(22) Filed: Nov. 16, 2018

(65) Prior Publication Data

US 2019/0142349 A1 May 16, 2019

Related U.S. Application Data

(60) Provisional application No. 62/737,070, filed on Sep. 26, 2018, provisional application No. 62/587,356, filed on Nov. 16, 2017.

(51) Int. Cl.
*A61B 5/00* (2006.01)
*A61B 5/11* (2006.01)
(Continued)

(52) U.S. Cl.
CPC .............. *A61B 5/7282* (2013.01); *A61B 5/11* (2013.01); *A61B 5/389* (2021.01); *G06F 3/015* (2013.01); *A61B 2560/0247* (2013.01)

(58) Field of Classification Search
CPC ............................ A61B 5/7282; A61B 5/0488
See application file for complete search history.

(56) References Cited

U.S. PATENT DOCUMENTS

| 4,106,063 A | * | 8/1978 | Lackner | H04N 5/94 360/55 |
| 6,132,387 A | * | 10/2000 | Gozani | A61B 5/0488 600/554 |

(Continued)

*Primary Examiner* — Daniel L Cerioni
*Assistant Examiner* — Yasmeen S Warsi
(74) *Attorney, Agent, or Firm* — Jenei LLC

(57) ABSTRACT

A system includes a processor in communication with a set of bioelectrical sensors and a user interface device that provides functionality to monitor one or more bioelectrical signals from a set of bioelectrical electrodes. Processor automatically adjusts a selected one of: (i) a resting threshold; and (ii) a switch threshold that is greater than the resting threshold based at least in part on a trend of the bioelectrical signal. The processor determines whether an amplitude of the bioelectrical signal is less than the resting threshold. In response to determining that the amplitude is less than the resting threshold, the processor determines whether an amplitude of the bioelectrical signal subsequently is equal to or greater than the switch threshold. In response to determining that the bioelectrical signal is greater than the switch threshold, the processor triggers the user interface device with a switch signal. The present disclosure illustrates various techniques and configurations to enable a series of dynamic workflows for the selection and presentation of content from an information system relevant to activities of a human user. The dynamic workflows used with the NeuroNode as described herein enable the integration of user interfaces and user communication platforms to achieve relevant and timely communication among users and others and related actions. The dynamic workflows described herein further may be integrated with social networks and portable communication mediums to provide additional availability and delivery of content to users in a variety of settings.

18 Claims, 16 Drawing Sheets

(51) Int. Cl.
*G06F 3/01* (2006.01)
*A61B 5/389* (2021.01)

(56) References Cited

U.S. PATENT DOCUMENTS

| | | | | |
|---|---|---|---|---|
| 2005/0012715 | A1* | 1/2005 | Ford | G06F 3/015 |
| | | | | 345/158 |
| 2006/0270943 | A1* | 11/2006 | Kamataki | A61B 5/0488 |
| | | | | 600/554 |
| 2009/0171417 | A1* | 7/2009 | Philipson | A61N 1/36003 |
| | | | | 607/48 |
| 2016/0082277 | A1* | 3/2016 | Foshee, Jr. | A61N 1/39 |
| | | | | 607/5 |
| 2016/0125705 | A1* | 5/2016 | Hurtig | G06F 3/017 |
| | | | | 340/4.11 |

* cited by examiner

ELECTROMYOGRAPHY (EMG) ASSISTIVE COMMUNICATIONS DEVICE WITH CONTEXT-SENSITIVE USER INTERFACE

CROSS-REFERENCE TO RELATED APPLICATIONS

The present Application for Patent claims priority to U.S. Provisional Application No. 62/587,356 entitled "ELECTROMYOGRAPHY (EMG) ASSISTIVE COMMUNICATIONS DEVICE" filed 16 Nov. 2017, and to U.S. Provisional Application No. 62/737,070 entitled "ELECTROMYOGRAPHY (EMG) ASSISTIVE COMMUNICATIONS DEVICE WITH CONTEXT-SENSITIVE USER INTERFACE" filed 26 Sep. 2018, both of which are hereby expressly incorporated by reference herein.

BACKGROUND

1. Technical Field

The present disclosure generally relates to bioelectrical switch controls and more particularly to electromyography-based switching systems having an artificial intelligent interface.

2. Description of the Related Art

Various types of injuries and diseases can limit the ability of an affected person with controlling various kinds of user interfaces. Such conditions include amyotrophic lateral sclerosis (ALS), also known as Lou Gehrig's disease, motor neuron disease (MND), spinal cord injury (SCI), or cerebral palsy (CP). Alternative/augmentative communication (AAC) technologies are increasingly becoming available that can provide a measure of control to some but not all of these individuals. In particular, some degree of control is provided by eye tracking devices, blow tubes, a face actuated toggle switch, etc. However, some individuals lack sufficient controllable movement to use such AAC technologies. Devices on the Assistive Technology (AT) market do not adjust over time to the user's abilities. In a matter of months, for example, an ALS patient can lose speech and motor control that were available when a device was first adopted. Other users may experience a significant drop in motor abilities over the span of a single session due to fatigue.

Attempts at expanding the number of people who can use AAC include use of bioelectrical signals. A motor unit is defined as one motor neuron and all of the muscle fibers that the one motor neuron innervates. When a motor unit fires, the impulse (called an action potential) is carried down the motor neuron to the muscle. The area where the nerve contacts the muscle is called the neuromuscular junction, or the motor end plate. After the action potential is transmitted across the neuromuscular junction, an action potential is elicited in all of the innervated muscle fibers of that particular motor unit. The sum of all this electrical activity from multiple motor units, the signal typically evaluated during electromyography, is known as a motor unit action potential (MUAP). This electrophysiological activity measures muscle response or electrical activity in response to a nerve's stimulation of the muscle. The composition of the motor unit, the number of muscle fibers per motor unit, the metabolic type of muscle fibers and many other factors affect the shape of the motor unit potentials in the myogram.

Generally known systems for using bioelectrical signals are labor intensive, requiring extensive setup time and frequent adjustments by a trained clinician in order to provide a usable system. Each individual can have a markedly different range of bioelectrical signals as compared to another person. Even the same person can have a wide variation in the characteristics of the bioelectrical signals as the person becomes tired. Moreover, certain individuals can have a complicated response including involuntary spasms that may lead to false switching signals.

BRIEF SUMMARY

In one aspect, the present disclosure provides a method that includes monitoring a bioelectric signal from a set of electrodes placed on a user. The method includes automatically adjusting a selected one or both of: (i) a resting threshold; and (ii) a switch threshold that is greater than the resting threshold based at least in part on a trend of the bioelectric signal. A determination is made as to whether an amplitude of the bioelectrical signal is less than the resting threshold. In response to determining that the amplitude is less than the resting threshold, a further determination is made as to whether an amplitude of the bioelectrical signal subsequently is equal to or greater than the switch threshold. In response to determining that the bioelectrical signal is greater than the switch threshold, the method includes triggering a device with a switch signal.

In another aspect, the present disclosure provides a system that includes a processor in communication with a set of bioelectrical sensors and a user interface. The processor provides functionality to monitor a bioelectrical signal from the set of bioelectrical electrodes. The processor automatically adjusts a selected one or both of: (i) a resting threshold; and (ii) a switch threshold that is greater than the resting threshold based at least in part on a trend of the bioelectrical signal. The processor determines whether an amplitude of the bioelectrical signal is less than the resting threshold. In response to determining that the amplitude is less than the resting threshold, the processor determines whether an amplitude of the bioelectrical signal subsequently is equal to or greater than the switch threshold. In response to determining that the bioelectrical signal is greater than the switch threshold, the processor triggers the user interface device with a switch signal.

In another aspect, the present disclosure illustrates various techniques and configurations to enable a series of dynamic workflows for the selection and presentation of content from an information system relevant to activities of a human user. The dynamic workflows used with the NeuroNode as described herein enable the integration of user interfaces and user communication platforms to achieve relevant and timely communication among users and others and related actions. The dynamic workflows described herein further may be integrated with social networks and portable communication mediums to provide additional availability and delivery of content to users in a variety of settings.

The above summary contains simplifications, generalizations and omissions of detail and is not intended as a comprehensive description of the claimed subject matter but, rather, is intended to provide a brief overview of some of the functionality associated therewith. Other systems, methods, functionality, features and advantages of the claimed subject matter will be or will become apparent to one with skill in the art upon examination of the following figures and detailed written description.

BRIEF DESCRIPTION OF THE DRAWINGS

The description of the illustrative embodiments can be read in conjunction with the accompanying figures. It will be appreciated that for simplicity and clarity of illustration, elements illustrated in the figures have not necessarily been drawn to scale. For example, the dimensions of some of the elements are exaggerated relative to other elements. Embodiments incorporating teachings of the present disclosure are shown and described with respect to the figures presented herein, in which.

DETAILED DESCRIPTION

Figure 1:
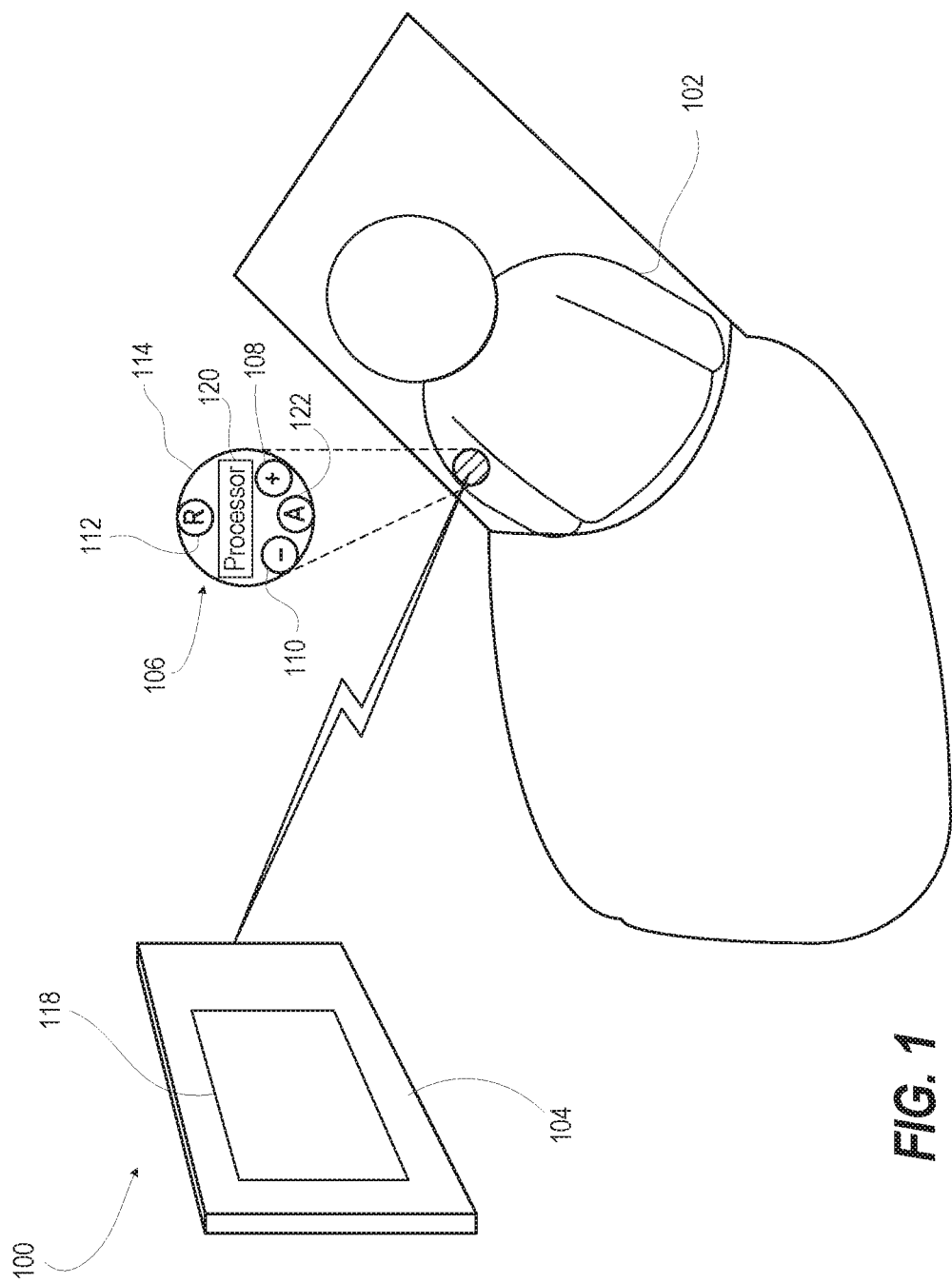
FIG. 1 illustrates a diagram of a NeuroNode system 100 enabling a user to control a device, such as a user interface device, according to one or more embodiments.

The embodiments of the present invention described below are not intended to be exhaustive or to limit the invention to the precise forms disclosed in the following detailed description. Rather, the embodiments are chosen and described so that others skilled in the art may appreciate and understand the principles and practices of the present invention.

While exemplary embodiments incorporating the principles of the present invention have been disclosed herein above, the present invention is not limited to the disclosed embodiments. Instead, this application is intended to cover any variations, uses, or adaptations of the invention using its general principles. Further, this application is intended to cover such departures from the present disclosure as come within known or customary practice in the art to which this invention pertains.

As used herein, the term "client application" refers to an application that runs on a client computing device. A client application may be written in one or more of a variety of languages, such as C, C++, C #, J2ME, Java, ASP.Net, VB.Net and the like. Browsers, email clients, text messaging clients, calendars, and games are examples of client applications. A mobile client application refers to a client application that runs on a mobile device. As used herein, the term "network application" refers to a computer-based application that communicates, directly or indirectly, with at least one other component across a network. Web sites, email servers, messaging servers, and game servers are examples of network applications.

As utilized herein, the terms "component," "computer component," "system," "client" and the like are intended to refer to a computer-related entity, either hardware, software (e.g., in execution), firmware, or a combination thereof. For example, a component can be a process running on a processor, an object, an executable, a program, a function, a library, a subroutine, a computer, or a combination of software and hardware. By way of illustration, both an application running on a server and the server can be a component. One or more computer components can in various embodiments reside on a server and the server can be comprised of multiple computer components. One or more computer components are in some cases referred to as computer systems whereby one or more computer components operate together to achieve some functionality. One or more computer components can reside within a process or thread of execution and a computer component can be localized on one computer or distributed between two or more computers.

The term "controller" as used herein indicates a method, process, or computer component adapted to affect a user device (i.e., the system to be controlled or effected).

As used herein, the term "electrode" means an operable connection to a muscle or nerve that allows an electrical potential so to be recorded or applied. An electrode can be further described by its location, i.e., internal, external or percutaneous; electrical or other recording characteristics, i.e., unipolar, bipolar, laptacian, magnetic or optical; and with respect to internal electrodes by its placement, i.e., intramuscular, epimysial, or nerve.

The term "electronic device" is used to designate any devices that can have a microprocessor and that can be communicated with. A microprocessor can include one or more processors, memory and programmable input/output peripherals. A controller can include one or more microprocessors and/or memory with instructions that can help control or communicate with electronic devices.

As used herein, when the term "function" is used to describe a relationship between one variable or parameter and a second variable or parameter, the relationship so described is not considered to be an exclusive relationship unless expressly stated, rather the other variables or parameters that are not mentioned or described but that are known to those of ordinary skill in the art may also have a functional relationship to the second variable or parameter. By way of example, if x is described as a function of y the statement is not intended to limit x's value to only being described by y unless expressly stated, rather the variable x may also be a function of other variables (e.g., x=f(y, t)).

"Intelligent Agent" is an autonomous computer program that carries out tasks and directs its activity towards achieving goals. Intelligent agents may learn or use knowledge from the environment, humans, and/or data sources to achieve their goals. Intelligent "agents" may also be referred to as "assistants" and/or "administrators." "Adaptive" means that an intelligent agent makes decisions on the basis of rules and can modify the rules on the basis of new information that becomes available.

As used herein, the term "Non-volatile memory," "NVM, or "non-volatile storage" means a type of computer memory that can retrieve stored information even after having been power cycled. In contrast, volatile memory needs constant power in order to retain data. Examples of non-volatile memory include read-only memory, flash memory, ferroelectric RAM, most types of magnetic computer storage devices (e.g. hard disk drives, solid state drives, floppy disks, and magnetic tape), optical discs, and early computer storage methods such as paper tape and punched cards. Non-volatile memory can be classified as traditional non-volatile disk storage, or storage in non-volatile memory chips, e.g., EEPROM, SSD, NAND, etc.

An "operable connection" is one in which signals or actual communication flow or logical communication flow may be sent or received. Usually, an operable connection includes a physical interface, an electrical interface, or a data interface, but it is to be noted that an operable connection may consist of differing combinations of these or other types of connections sufficient to allow operable control.

The term "processor" is generally understood to refer to a hardware component, such as a processing unit of a computer system.

As described herein, the term "sensor" may include one or more electrodes or sensor electronics (e.g., in a processor or other circuitry) configured to acquire signals and to process the acquired signals in an analog domain, a digital domain or both. A sensor may comprise electrodes and associated sensor electronics integrated into a common structure such as an electrode pad or may comprise electrodes and sensor electronics that are disposed remotely from one another, such as electrodes coupled to a remotely positioned processor (e.g., positioned at another location on a user or garment) or other circuitry using an electrically conductive structure such as a conductive trace, wire, cable, or the like, for example. Biopotential sensors may include but are not limited to electromyography (EMG) sensors, ECG sensors, respiration, galvanic skin response (GSR), or others. Other types of sensors may also be incorporated into the devices described herein. These sensors may include but are not limited to accelerometers (single or multi-axis), GPS sensors, galvanic skin response (GSR), bioimpedance, gyroscopes, bend-angle measurement (flex) sensors (to measure joint angle or joint angles), etc.

As used herein, the terms "signal" may take the form of a continuous waveform or discrete value(s), such as electrical potentials, electrical currents, magnetic fields, optical fields, or digital value(s) in a memory or register, present in electrical, optical or other form.

The term "state" as used herein refers to a set of variables that define the characteristics of a particular system in a specific combination. In one non-limiting example, the state of a single axis, hinged joint is expressed as a vector comprised of the current angle, angular velocity and angular acceleration. In other aspects the state of a system includes otherwise unmeasurable or practically unobservable values.

The present innovation provides a controller that switches from on/off based on set parameters to control one of a wide variety of electronic devices. A prototype control device comprises (a) an electromyography (EMG) sensor and (b) an accelerometer. In one or more embodiments, a control device can utilize just one of the sensors. The EMG sensor can sense volitional electrical potential in muscles collected via an electrode. For example, the volitional electrical signal may incompletely innervate a muscle and thus not have the ability to trigger enough motor units to cause a physically manifest contraction of the muscle. However, this sub-functional activation of motor units within the muscle does result in measurable electromyography (EMG) signals.

In one or more embodiments, the device receives data input form one or more sensors. One or more embodiments can utilize standard electrocardiogram (EKG) electrodes. The device can be in multiple pieces or a unitary product. The electrodes can be attached directly to the unit body, wirelessly coupled, or connected by electrical leads. Other sensors may be utilized in the system, such as a proximity sensor, photodetector, a Hall-effect sensor, a radio frequency identifier (RFID) sensor, a biomedical sensor (such as electromyography, a moisture sensor, a fluid sensor, a temperature sensor, an electrodermal activity sensor, a chemical presence sensor, a biological presence sensor, sound sensor, vibration sensor, and a pH level sensor), a force sensor that may sense a mechanical force such as a pressure sensor or a flex sensor.

In one or more embodiments, the sensor can be an activity sensor, which generates a signal indicative of patient activity (e.g., patient movement or patient posture transitions). For example, an activity sensor may include one or more accelerometers, such as one or more single-axis, two-axis or three-axis accelerometers, capable of detecting static orientation or vectors in three-dimensions. An example accelerometer is a micro-electromechanical accelerometer. In other examples, an activity sensor may alternatively or additionally include one or more gyroscopes, pressure transducers, piezoelectric crystals, or other sensors that generate a signal that changes as a function of patient activity. In some examples, patient activity may also be detected via one or more EMG sensors that generate an electrical signal indicative of muscle movement or one or more intracranial pressure sensor that indicate a change in pressure in cranium, which may result from changes in patient posture or a change in patient activity level.

In one or more embodiments, the volitional electrical potential is used by the controller as a logical control input. A logical control or triggering command resembles a digital logic or on/off signal. In the case of a volitional electrical potential, the on/off signal is tailored to change state upon the user applying the volitional electrical potential.

One of the initial steps to the process is identifying which muscles and nerves of the user are still controlled by the user and capable of generating volitional electrical signals. An initial mapping process for identifying muscles and nerves where a user is capable of generating measurable, but still sub-functional volitional electrical potential, can be an initial starting point for tailoring the neural controller for a variety of users.

The NeuroNode uses the body's bioelectrical EMG signals to completely control a computer to generate speech, browse the web, listen to music, and more. In one or more embodiments, the present innovations address particular needs of users that have difficulty controlling a device using a bioelectrical signal. Some patients, for example those with cerebral palsy (CP), have spasms that can make it hard to differentiate what is intended as a Switch and what is a spasm. Spasms most often are accompanied by gross motor movement. By using accelerometer data, this gross movement can be recognized and used to disallow a Switch, even if the EMG activity otherwise would be considered a switch. Accelerometer data filtering can be by some combination of discrete x, y, and z data, or the algorithm can be by a simple product of x, y, and z; that is, if the product of x, y, z is greater than some user-selected limit, do not allow a switch.

The present invention provides user interface concepts, principles and techniques that can be translated into software algorithms to provide a rich functionality, convenience, flexibility and ease-of-use to users. Further, the disclosed concepts/principles/techniques can lead to easier implementation of the gesture recognition algorithms. Note that these concepts, techniques and principles can be used with controllers described elsewhere as well as any other devices that can track user's head/face/bodily motions, facial expressions and gestures to control or communicate with any electronic devices. Further, the UI concepts described herein can be used to not only control an electronic device distinct from the controller, but also the controller and/or the controlling system itself. For the purpose of simplicity, the rest of the document will use the term "controller" to include "controlling systems" as well. Further, it is also understood that controllers themselves can be electronic devices; therefore, any mention of "controlling/communicating with an electronic device" can also include controlling/communicating with the controller itself.

Embodiments of the disclosed technology provide reliable and fast communication of a human through an interface, which detects the intent of the user. Embodiments of the disclosed technology enable people with severe speech and motor impairments to interface with computer systems for the purpose of typing in order to establish and maintain seamless spontaneous communication with partners in face-to-face situations, as well as in remote environments such as Internet chat, email, or telephone (via text-to-speech). In addition, embodiments also enable the target population to access information available on the Internet through a computer. In an embodiment, healthy humans may also utilize the proposed interface for various purposes.

The systems and methods of the present invention are adaptable and, in some embodiments, can include additional sensors for multiple applications. In some embodiments, the systems and methods of the present invention can be integrated with, for example and not limited to, electro-oculogram (EOG), microphones, accelerometers, gyroscopes, miniature cameras, and flow and/or pressure sensors, as well as electropalatography, electromyography (EMG) and electroencephalography (EEG) electrode arrays for detecting tongue contact with the palate, muscle movement and/or activity, and brain activity.

The present disclosure includes various exemplary embodiments of systems and methods that utilize the location and context of a user and other resources to a) adjust to the current situation, b) prevent high risk situations, and/or c) respond to and manage situations. Various embodiments include collecting, aggregating, and analyzing user-related data specific to that user's condition, motivations, and usage. Such data/information can be collected from a wide variety of sensors and other data sources, including but not limited to: personal devices such as smartphones, tablets, computers, PDAs, wearables (data collection devices worn on the person, such as Fitbit, etc.), implants, Google GLASS, etc.; nearby sensors or devices such as security/video cameras, smart devices (such as smart home-related sensors, etc.), crowdsourcing data collection applications of nearby users, building/store/office Wi-Fi networks, location-sensitive beacons, etc.; and/or extended data collection mechanisms such as road traffic sensors, public video cameras or billboard displays, weather data collection sensors, law enforcement/security-related devices, etc.

In one or more embodiments, an example communications network includes a plurality of heterogeneous, differing, or different types of sensing devices configured to monitor the location and/or context of a user; and a plurality of heterogeneous, differing, or different types of interface devices each configured to engage in interaction with the user, with a support person for the user, and/or with a third party in the event that the network detects a relationship between the monitored location and/or context and a trigger predetermined in the network for the user; wherein the interaction is selected based on the trigger and the monitored location and/or context. The example communications network may include one or more server, client, cloud, peer-to-peer, and/or other devices configured to develop and/or update a profile of the addict based on monitoring data from the sensing devices and/or the interaction engaged in by one or more of the interface devices.

The system can operate in a home, a nursing home, a hospital or other setting. In one or more embodiments, the system includes one or more mesh network appliances to enable wireless communication in the home monitoring system. Appliances in the mesh network can include home security monitoring devices, door alarm, window alarm, home temperature control devices, fire alarm devices, among others. Appliances in the mesh network can be one of multiple portable physiological transducer, such as a blood pressure monitor, heart rate monitor, weight scale, thermometer, spirometer, single or multiple lead electrocardiograph (ECG), a pulse oxymeter, a body fat monitor, a cholesterol monitor, a signal from a medicine cabinet, a signal from a drug container, a signal from a commonly used appliance such as a refrigerator/stove/oven/washer, or a signal from an exercise machine, such as a heart rate. In one example, a user may have mesh network appliances that detect window and door contacts, smoke detectors and motion sensors, video cameras, key chain control, temperature monitors, CO and other gas detectors, vibration sensors, and others. A user may have flood sensors and other detectors on a boat. A user may have access to a panic transmitter or other alarm transmitter. Other sensors and/or detectors may also be included.

An embodiment of the disclosed technology may comprise one or more of the following components: (1) rapid serial presentation of stimuli, such as visual presentation of linguistic components (e.g., letters, words, phrases, and the like) or non-linguistic components (e.g., symbols, images, and the sort), or other modalities such as audible presentation of sounds, optionally with individual adjustment of presentation rates, (2) a user intent detection mechanism that employs multichannel electroencephalography (EEG), electromyography (EMG), evoked-response potentials (ERP), input buttons, and/or other suitable response detection mechanisms that may reliably indicate the intent of the user, and (3) a sequence model, such as a natural language model, with a capability for accurate predictions of upcoming stimuli that the user intends in order to control the upcoming sequence of stimuli presented to the subject.

In an embodiment of the disclosed technology, there is provided an optimal real-time, causal predictive, open-vocabulary, but context-dependent natural language model to generate efficient sequences of language components that minimize uncertainty in real-time intent detection. An embodiment provides accurate probabilistic large-vocabulary language models that minimize uncertainty of upcoming text and exhibit high predictive power, with sub-word features allowing for open-vocabulary use. In an embodiment, there are provided learning techniques integrated in the systems that allow perpetual, on-line adaptation of the language models to specific subjects based on previously input text. In addition, an embodiment provides optimal presentation sequence generation methods that help minimize uncertainty in intent detection and minimize the number of symbols presented per target.

The principles disclosed can be used with hand held and body worn controllers as well as with control systems where the user's body or body part is used as part of the control system. Body parts used for user actions prescribed to perform user gestures can include, but are not limited to, head, facial muscles, part of the face, jaws, tongue, eyes, fingers, hands, arms, torso, chest, abdomen, shoulders, legs, feet, toes and muscles.

A user gesture can be defined as a combination of actions performed (by the user) with the intent of communicating with or controlling an electronic device. These actions can be bodily actions that can include motions of various body parts, facial expressions, actions to orient and hold various body parts in certain poses/positions/orientations, as well as other bodily actions. Holding the eye gaze steady or moving the eye gaze can also be considered a bodily action. Some embodiments can also use actions performed by the user such as speech/speaking, holding breath/inhaling/exhaling, tensing of muscles/body parts (that may or may not be detected externally, such as jaw muscles, abdominal muscles, arm and leg muscles, anal sphincter, etc.), and so on as bodily actions. User actions such as entering meditative or attentive state, consciously relaxing the body with or without meditation, (mentally) imagining, visualizing, remembering or intending particular actions (e.g. pushing or pulling, lifting or lowering imaginary, virtual or real objects), experiences or scenarios (which can be detected by analyzing brainwaves or other biometric information), deep breathing, inhaling, exhaling, holding breath, etc. can also be used as actions in defining user gestures. A user gesture can require some bodily actions to be performed in a specified sequence and can require other bodily actions to be performed concurrently/simultaneously with each other. User gestures can be recognized and translated by the controller or control system into signals to communicate with and/or control an electronic device. Some user gestures can be recognized and translated into signals to control the controller/control system itself. Signals generated in response to some user gestures may be stored in the control system or controlled device for indefinite amount of time and that stored signal information can be retrieved when required. Bodily actions performed as part of a user gesture can serve various purposes in a specified user gesture. Following are some types of bodily actions based on the purpose they can fulfill in a user gesture.

A particular bodily action can serve different purposes (and thereby can be viewed as having different types) when it is used in different types of user gestures. Further, a particular bodily action can occur multiple times within a user gesture and can be specified to have different purpose(s) (type/types) during different occurrences.

Any particular heuristics can be implemented in a controller/control system by means of multiple user gestures. For example, the selection heuristics can be implemented in one embodiment using a first user gesture that uses a smile facial expression as the Primary Control Expression (PCE) as well as another user gesture that uses an eyebrow raise facial expression as the PCE, and so on.

One challenge that users with spasms have with switching technology is "false" switches. False Switches are cases where spasms are recognized by the NeuroNode as an EMG switch. By setting the sensitivity of "Switch Disable," various levels of movement captured by the accelerometer can be used to disallow a NeuroNode Switch. The Switch Disable Threshold can be programmed by some discrete combination of x, y, and z data, or by the x, y, z product.

In one or more embodiments, an accelerometer switch mode can be used with EMG or without. In this mode, the patient and clinician record the x, y, z, and EMG (optional) components of a patient movement. This "Signature" is set as a switch for the NeuroNode. When movements with characteristics that are similar to the Signature are detected, the NeuroNode allows that this is a switch. The sensitivity of the Switch, that is, how close the movement follows the original signature, can be programmed.

In one or more embodiments, context sensitive switching can be incorporated, such as when the system learns more about the user or has additional associations supplied. Switch scanning is usually slower than direct select methods like eye tracking (or mousing or keyboarding, if the user has that level of function). To "even the score," the present innovation contemplates methods for improving the speed of switch scanning such as context sensitive switching. Inputs are gathered that add context to the patient's situation. These inputs can be used an appropriately tailored "chat panel" on the display. For example, with a combination of a time-of-day clock and a proximity detector, the application can put up a chat panel that related to a discussion of school when the patient's daughter enters the room at 4:00 pm on a weekday. As another example, if the temperature in the room moves outside of the patient's comfort range, a chat panel related to environmental control can be programmed to appear. For example, if you know the nurse stops in every Tuesday at 11 am, then at that time, a menu comes up with a variety of pre-selected responses that relate to a nurse visit. If a spouse comes home at 5 pm every day, a menu for that could come up every day at 5 pm. Thus, instead of the patient switching through a sometimes deep hierarchy of chat panels, the NeuroNode with context sensitive switching can anticipate what the user (patient) wants to say or do.

In one or more embodiments, the present innovation can provide both dynamic and static scaling modes. Static scaling imposes fixed criteria that the EMG signal must satisfy in order to be counted as a Switch. These criteria remain unchanged over time. Dynamic scaling changes the criteria over time for determining if a switch has been made based on the user's performance. In one or more embodiments, the EMG resting level and the EMG signaling level are both used in this ongoing calculation. As such, the NeuroNode will make it easier to Switch as the user fatigues, or as other electrode interface conditions change. In one or more embodiments, a physiological reading off of the user's body or accelerometer resting level and the a physiological reading off of the user's body or accelerometer signaling level are both used in this ongoing calculation. As such, the NeuroNode will make it easier to Switch as the user fatigues, or as other electrode interface conditions change.

Dynamic threshold amplitude can set a scale factor for use by the NeuroNode's dynamic scaling algorithm. The lower the percentage as it approaches 100%, the more sensitive the NeuroNode will be in allowing that the EMG signal is a switch. Threshold amplitude (static scaling) sets the EMG amplitude the signal must cross above in order to be counted as a switch. Threshold amplitude (dynamic scaling) sets a scale for use when in the NeuroNode's dynamic scaling mode. The lower the level, the more sensitive the NeuroNode will be in allowing a switch to be made.

The Signal Off parameter is pre-set in the Static Scaling mode and computed continuously in the Dynamic Scaling mode. Signal off Amplitude sets the EMG amplitude a signal counted as a Switch must fall below before a new Switch can be counted. Setting this parameter at the same level as the Threshold Amplitude will remove Signal off amplitude as a switching determiner.

A parameter, Signal Off, was created to address the problems of spasms, fasciculation, and high muscle tone. Signal Off is pre-set in the Static Scaling mode and computed continuously in the Dynamic Scaling mode. Signal Off is used to disallow any additional Switches after the first one until the signal level drops below the Signal Off amplitude.

Dynamic Signal Off Amplitude sets the level a Switch signal must drop below before another Switch is allowed. Setting this at 100% will set the Signal Off Amplitude to the user's ongoing average Resting Level. Setting this parameter at the same percentage as Threshold Amplitude will remove Signal Off as a Switching determiner.

Dynamic Scaling changes the criteria over time for determining if a switch has been made based on the user's performance. In one or more embodiments, the Dynamic Scaling may make use of EMG resting level and the EMG signaling level in this ongoing calculation. In one or more embodiments, the Dynamic Scaling may make use of the resting level and the signaling level of one or more sensors on the user's body such as a physiological sensor or accelerometer for motion detection in this ongoing calculation. As such, the NeuroNode will make it easier to switch as the user fatigues, or as the electrode interface conditions change.

In the following detailed description of exemplary embodiments of the disclosure, specific exemplary embodiments in which the disclosure may be practiced are described in sufficient detail to enable those skilled in the art to practice the disclosed embodiments. For example, specific details such as specific method orders, structures, elements, and connections have been presented herein. However, it is to be understood that the specific details presented need not be utilized to practice embodiments of the present disclosure. It is also to be understood that other embodiments may be utilized and that logical, architectural, programmatic, mechanical, electrical and other changes may be made without departing from general scope of the disclosure. The following detailed description is, therefore, not to be taken in a limiting sense, and the scope of the present disclosure is defined by the appended claims and equivalents thereof.

References within the specification to "one embodiment," "an embodiment," "embodiments," or "one or more embodiments" are intended to indicate that a particular feature, structure, or characteristic described in connection with the embodiment is included in at least one embodiment of the present disclosure. The appearance of such phrases in various places within the specification are not necessarily all referring to the same embodiment, nor are separate or alternative embodiments mutually exclusive of other embodiments. Further, various features are described which may be exhibited by some embodiments and not by others. Similarly, various requirements are described which may be requirements for some embodiments but not other embodiments.

It is understood that the use of specific component, device and/or parameter names and/or corresponding acronyms thereof, such as those of the executing utility, logic, and/or firmware described herein, are for example only and not meant to imply any limitations on the described embodiments. The embodiments may thus be described with different nomenclature and/or terminology utilized to describe the components, devices, parameters, methods and/or functions herein, without limitation. References to any specific protocol or proprietary name in describing one or more elements, features or concepts of the embodiments are provided solely as examples of one implementation, and such references do not limit the extension of the claimed embodiments to embodiments in which different element, feature, protocol, or concept names are utilized. Thus, each term utilized herein is to be given its broadest interpretation given the context in which that term is utilized.

FIG. 1 illustrates a NeuroNode system 100 for enabling a user 102 to control a device, such as a user interface device 104. The NeuroNode system 100 gives the user complete control over the NeuroNode system 100 without requiring extensive computer experience. Here are just a few examples of what persons with paralysis, loss of speech, or loss of motor control can do with the NeuroNode system 100: Communicate with family, caregivers, and clinicians using text-to-speech (TTS); send text messages and email; surf the web; watch videos and movies; listen to music, radio, and podcasts; read the news; play video games; use environmental controls; and participate in the classroom using telepresence robots and assistive technology.

The NeuroNode system 100 includes a set of bioelectrical electrodes 106. In one or more embodiments, a first active electrode 108, a second active electrode 110 and a reference ("R") electrode 112 are attachable to an electrode device ("NeuroNode device") 114 that is adhered to the user 102. In other embodiments, each electrode 108, 110, 112 is individually adhered to the user 102 and interfaced to the system 100 such as via electrical leads or a wireless connection. A processor 120, such as contained in the NeuroNode device 114 or in the user interface device 104, is in communication with the set of bioelectrical sensors 106 and the user interface device 104 that projects functionality for an application 118 executed on the user interface device 104. The NeuroNode device 114 includes a processor 120 that supports dynamic and static adjustments to switching threshold that accommodate specific requirements of the user 102 as compared to other individuals or as compared to changing characteristics of the user 102.

In one or more embodiments, NeuroNode device 114 is a mesh accessible surface electromyography controller, wearable by a user 102, for capturing electromyography and electrocardiography data from certain muscles, including the heart. NeuroNode device 114 has the ability to store the data onboard for extended periods, and to send the data by Bluetooth or Wi-Fi or other wireless means to a receiver. The NeuroNode device 114 can analyze the data onboard or send data to a receiver for analysis by code or by a person. When analyzing the data onboard, the NeuroNode device 114 can assess certain intentions of the user 102, such as sending a command to the receiver to perform any of a range of tasks including displaying text, broadcasting that text in the form of computer-generated speech, controlling programs and other software within the receiver as well as within other peripheral programs and devices. The NeuroNode device 114 monitors parameters and sensor systems and incorporates algorithms that continually adapt to the user's abilities. In addition, the system predicts what the user wants to say/do by gathering context from sensors and user behavior.

In an exemplary embodiment, the processor 120 performs an algorithm as follows:

```
With every 50 ms EMG_DATA_POINT {
    Place data point in an array of 5 seconds of data points =
    EMG_WINDOW
    Discard the oldest data point in EMG_WINDOW (the array always
    holds the last 5 seconds of EMG data)
    Iterate through EMG_WINDOW and store the EMG value of all
    peaks in PEAK_WINDOW
    Iterate through EMG_WINDOW and store the EMG value of all
    "pits" in PITS_WINDOW
    AVG_PEAK = average of peaks in PEAK_WINDOW
    AVG_PIT = average of pits in PITS_WINDOW
    THRESHOLD_AMPLITUDE = ((AVG_PEAK + AVG_PIT) / 2) *
    Sensitivity Scale Factor 1)
    SIGNAL_OFF = ((AVG_PEAK + AVG_PIT) / 2) * Sensitivity
    Scale Factor 2)
}
Use THRESHOLD_AMPLITUDE to determine if EMG_DATA_POINT
is an HID switch
```

Threshold Amplitude sets a scale for use when in the NeuroNode's Static and Dynamic Scaling Modes. The lower the level, the more sensitive the NeuroNode will be in allowing a Switch to be made.

For example, the NeuroNode device 114 can include an accelerometer ("A") 122 provides a collaborating input or alternate inputs to the electrodes 106. A movement that is characteristic of a spasm can be recognized by the processor 120 and can be used to ignore an otherwise qualifying bioelectric signal. A movement that is recognized as an expected volitional movement for a switch conversely can be relied upon on its own or as a confirmation of a qualifying bioelectrical signal. For example, adjusting the baseline for the bioelectrical signal can require that the accelerometer confirm a same pattern of movement, albeit more slight, as a previous accepted baseline.

In accordance with another embodiment of the invention, the complete NeuroNode system 100 can be an implantable device suitable for implantation in the body and comprising a set of bioelectrical electrodes 106. In one or more embodiments, a first active electrode 108, a second active electrode 110 and a reference ("R") electrode 112 are attachable to an electrode device ("NeuroNode device") 114 that is implanted in the user 102. In accordance with another embodiment of the invention, the bioelectrical electrodes 106 are suitable for implantation in the user 102 while attachable to an external NeuroNode device 114.

In accordance with another embodiment of the invention, there is provided a system for communicating intra-body signals generated by an implantable sensing device. In the context of data being communicated from within the body, transferred signals, generally referred to herein as "intra-body signals" are meant to include different signals representative of a condition, characteristic and/or parameter, directly or indirectly sensed or otherwise observed from within the body. In some examples, intra-body signals may include "biosignals," which are meant to include different signals representative of a sensed biological/physiological condition, characteristic and/or parameter, directly or indirectly sensed or otherwise observed from within the body. Such biosignals are described herein within the context of user/patient monitoring and/or diagnostics; however, it will be appreciated that embodiments of the invention described herein may be practiced for the transmission of data to be used for a variety of purposes or in a variety of contexts, which are therefore considered to fall within the scope of this disclosure. Similarly, different embodiments may also or alternatively consider the transfer of "environmental signals" meant to include different signals representative of an environmental condition, characteristic and/or parameter directly or indirectly sensed or otherwise observed from within the body, or again representative of an internal response of the body to such environmental conditions or characteristics. In yet other examples, such environmental signals may rather allow for a determination of the implanted body's position or movement.

As will be described in greater detail below, some embodiments of the invention rely on an effective data signal communication design and system implemented by, in some embodiments, a concise implantable data manipulation and transmission circuit or platform useable for the transmission of a variety of intra-body signals, in one or more data channels, from within the body to an external receiver. Accordingly, it will be appreciated that while different examples are considered herein in the context of medical monitoring and/or diagnostics via the manipulation of generally electric biosignals, used for example in the context of an electrocardiogram (ECG), electroencephalogram (EEG), electrocorticogram (ECoG), electromyogram (EMG), electro-oculogram (EOG), electrogastrogram (EGG), etc., other types of signals may also be considered. For instance, upon adding a transducer as part of the described systems, other non-electrical biological parameters such as blood pressure, body temperature, blood oxygen saturation ($SpO_2$), blood $CO_2$ saturation, NO concentration, respiration, and/or other types of physiological sensing systems, as will be readily appreciated by the skilled artisan, may be considered, whereby such sensed parameters are effectively converted by an appropriate implantable transducer or the like to generate an electrical signal representative thereof and readily transmittable using different embodiments of the invention, as described herein.

In other embodiments, environmental sensors are used instead of or in combination with biosensors, which environmental sensors may include, but are not limited to, gravitational sensors, magnetic field sensors, radiation sensors and the like. For instance, the implantation of such environmental sensors within the body may allow one to measure or evaluate a response of the body to such environmental conditions, detect an intensity or amplitude of environmental conditions within the body, or use such measurements to identify a position or movement of the body, for example. It will be appreciated by the skilled artisan in considering the following disclosure that other types of sensors and sensed characteristics may be considered herein without departing form the general scope and nature of the present disclosure.

Figure 2:
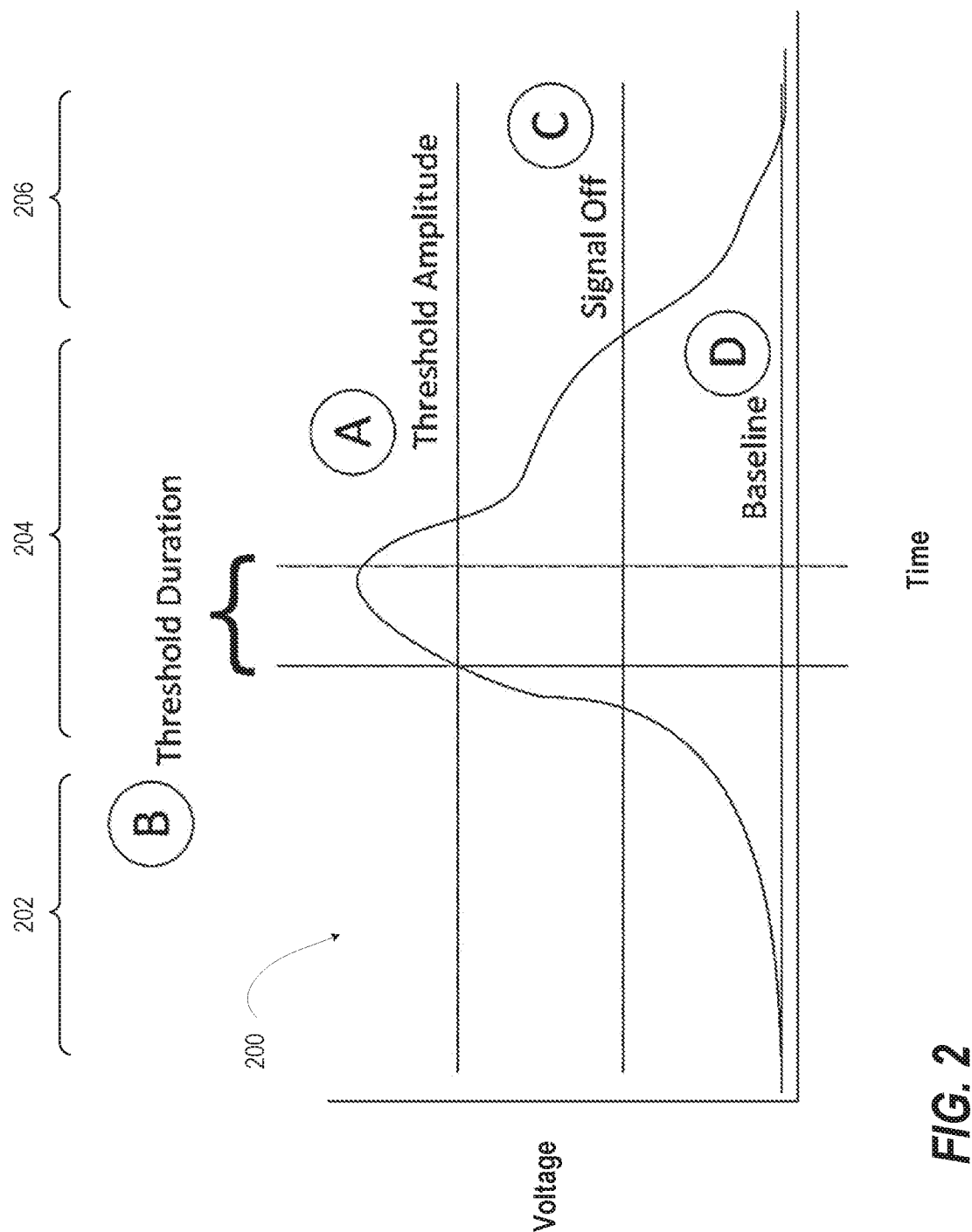
FIG. 2 illustrates a graph of a representative bioelectrical signal that is volitionally generated by a user, according to one or more embodiments.

FIG. 2 illustrates a graph of a representative bioelectrical signal 200 that is volitionally generated by a user. The signal 200 begins with a resting level 202, followed by switching level 204, which is then followed by another resting level 206. When the signal 200 reaches (A), a human interface device (HID) code is sent so long as the signal stays above (A) for a threshold duration (B). Another Switch code is not allowed until the signal 200 drops below a threshold level (C). Dropping below threshold (C) or another threshold such as baseline (D) can be required to reset monitoring for a subsequent triggering of an HID code (switch). In one or more embodiments, value (D) can be deemed the "0 point" for calculations rather than 0 amplitude/duration (A/D) units.

The triggering input determines whether or not to switch the state of the command signal from an initial state to a second state. In one embodiment, the initial state is a default state of the toggle switch (e.g., 0) corresponds to a baseline or no volitional electrical potential 102 generated by the user, while the complimentary state (e.g. 1) corresponds to an elevated level of volitional electrical potential, thus when the volitional electrical potential returns to baseline or zero level the toggle switches back to the default state (e.g. 0). In another embodiment, the triggering input causes only a state change from its current state to the next state (i.e., in the case of a binary switch toggling to the other state, e.g., from a 1 to a 0 or vice versa).

In embodiments with multiple state switches, when the volitional electrical potential exceeds the trigger state the switch state increments by a fixed amount (i.e., moving from the current mode to another mode). For example, in one aspect the switch state may possess three separate modes of operation, a first state corresponding to no stimulus, a second state corresponding to a specific pattern or other action applied, and third state corresponding to a second pattern or other action.

In other embodiments, multiple inputs are used by the controller to determine the user's desired action. In one exemplary embodiment, a first volitional electrical potential signal is used as a toggle input, where the action of the first volitional electrical potential signal is used to toggle the state of the controller from mode to mode. Then a second volitional electrical potential signal is used by the controller to actuate a second action. One of ordinary skill in the art can adapt the forgoing exemplary embodiment so scenarios with multiple volitional electrical potential signals or other EMG or external input devices (e.g., joysticks, buttons, voice input, etc.) can actuate multiple actions.

In one exemplary embodiment, the first action can represent a keyboard key pressed signal. The next state can represent the release of the key. In another exemplary embodiment, the controller utilizes the volitional electrical potential created by the user, in some cases in conjunction with other inputs such as EMG signals or input devices, to select, initiate and modulate pre-defined sequences of commands.

Figure 3:
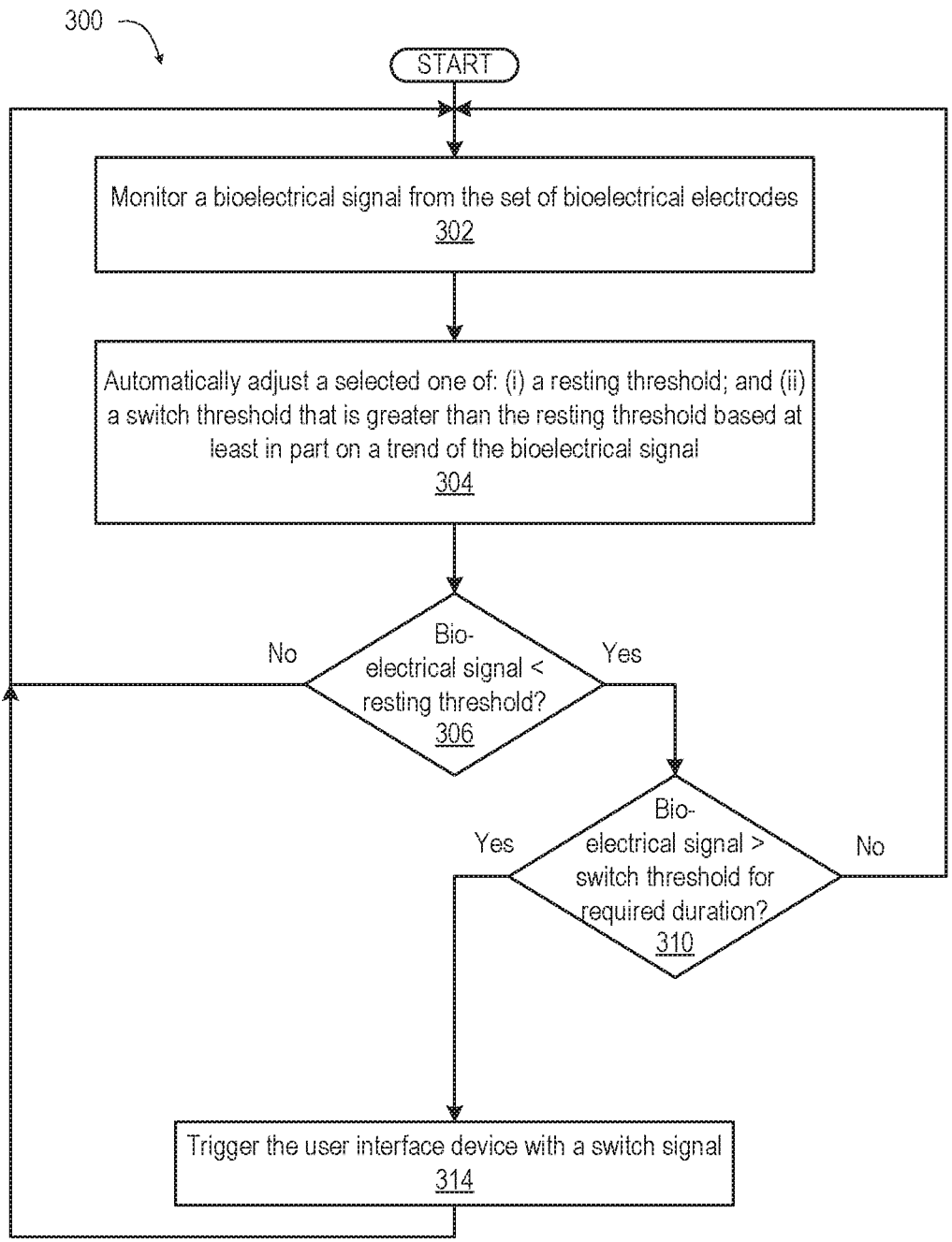
FIG. 3 is a flow diagram illustrating a method of controlling a device with bioelectrical monitoring, according to one or more embodiments.

FIG. 3 illustrates a method of controlling a device with bioelectrical monitoring. In one or more embodiments, method 300 includes monitoring a bioelectrical signal from the set of bioelectrical electrodes (block 302). Method 300 includes automatically adjusting a selected one of: (i) a resting threshold; and (ii) a switch threshold that is greater than the resting threshold based at least in part on a trend of the bioelectrical signal (block 304). Method 300 includes determining whether an amplitude of the bioelectrical signal is less than the resting threshold (decision block 306). In response to determining that the amplitude is not less than the resting threshold, method 300 returns to decision block 306 to continue monitoring for a reset based on being less than the resting threshold. In response to determining that the amplitude is less than the resting threshold in decision block 306, a determination is made as to whether an amplitude of the bioelectrical signal subsequently is equal to or greater than the switch threshold for a required duration (decision block 310). In response to determining that the bioelectrical signal is not greater than the switch threshold for at least required duration, method 300 returns to decision block 306 to continue waiting for conditions that represent a user commanded switch. In response to determining that the bioelectrical signal is greater than the switch threshold for at least required duration, method 300 includes triggering the user interface device with a switch signal, such as to interact with an application (block 314). Then method 300 returns to block 302.

In one or more embodiments, method 300 includes monitoring a movement sensor that is attached to the user, wherein triggering the device with the switch signal is further in response to determining that a movement signal sensed by the movement sensor concurrently with the bioelectrical signal is less than a spasm threshold.

In one or more embodiments, method 300 includes: (i) determining, by the device, whether a contextual trigger condition exists; (ii) in response to determining that the contextual trigger condition exists, presenting to the user an application that is associated with the contextual trigger condition; and (iii) controlling the application with the switch signal. In an exemplary embodiment, the contextual trigger condition is a chronological event. In another exemplary embodiment, the contextual trigger condition comprises an ambient environmental event and the application comprises an environmental control interface. In another exemplary embodiment, the contextual trigger condition is a detected third-party proximity event and the application comprises a human communication application.

Figure 4:
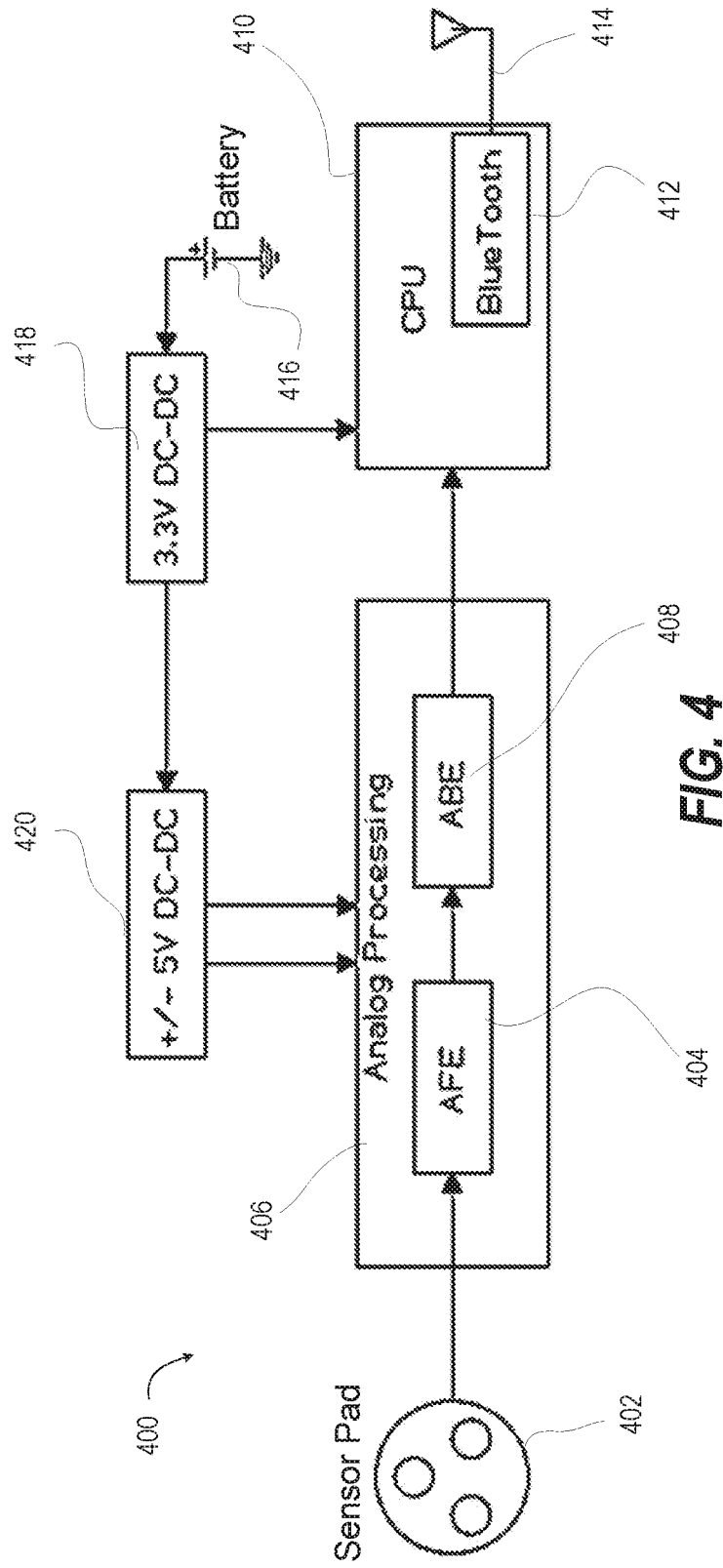
FIG. 4 is a functional block diagram illustrating an example NeuroNode device, according to one or more embodiments.

FIG. 4 illustrates an example NeuroNode device 400 having a sensor pad 402 that provides a signal to an analog front end (AFE) 404 of an analog processing component 406. The processed signal is relayed by an analog back end (ABE) 408 of the analog-processing component 406 to a central processing unit (CPU) 410. The CPU 410 performs intelligent coding that includes software to process and analyze EMG data and to produce and transmit data and commands. The CPU 410 generates an HID switch ON or switch OFF code that is relayed by a Bluetooth transceiver 412 over an antenna 414. Power for the NeuroNode device 400 is provided by a battery 416 that is converted by a 3.3 V DC-DC digital power supply 418 to support the CPU 410 and a +/−5 v DC-DC power supply 420 that supports the analog processing component 406. For example, battery 416 can be a LIR2032 80 mAh rechargeable coin cell battery or similar power source. Power supply 420 can be based on Linear Technology LT3582-5, boost and single inductor inverting DC/DC converter. Input range: 2.55 to 5.5 V.

Bluetooth transceiver 412 can be a Bluetooth semiconductor chip that can include Bluetooth Low Energy (BLE) capability to transmit and receive data and supports a mesh network of multiple NeuroNode devices 400 with one elected host to contact another device. Thus, each NeuroNode device 400, or similar units configured for monitoring a bioelectrical signal, determines a hierarchy of data flow in which one NeuroNode becomes the central controller and passes all data to and from each of the other NeuroNode units in the mesh network. This enables a number of NeuroNode units to be attached to a user so that all data and instructions are efficiently channeled through a single unit to and from other devices or software. Outbound data: data sent from the NeuroNode or mesh network can be sent in Boolean format (0 or 1, i.e., OFF or ON) or dynamic format such as a data stream to control switching software or hardware, or variable software (such as a cursor through X and Y coordinates on a screen) or hardware (such as a robotic device).

Target systems include software (such as programs that can be controlled by Boolean or dynamic data, including Assistive Technology programs); hardware (such as robotic systems which may include control and response software); firmware (such as resident software that controls a device such as a television, music or video player or recorder, smartphone, tablet, computer, environmental control system); proximity systems such as a Near Field Communication (NFC) system; analytical systems, such as a cardiography or other data analysis systems, pattern recognition systems or other data-based system; and programmed or artificial intelligence systems. The NeuroNode device 400 captures physiological data and stores, analyzes, transmits and uses the data and calculated results to display information, interface with other software and hardware systems, and control other devices.

The simplified device 400 shown in FIG. 4 may also include a variety of computer-readable media. Computer-readable media can be any available media that can be accessed by the CPU and can include both volatile and nonvolatile media that is either removable and/or non-removable, for storage of information such as computer-readable or computer-executable instructions, data structures, program modules, or other data. Computer-readable media includes computer storage media and communication media. Computer storage media refers to tangible computer-readable or machine-readable media or storage devices such as digital versatile disks (DVDs), Blu-ray discs (BD), compact discs (CDs), removable media or storage, tape drives, hard drives, optical drives, solid state memory devices, random access memory (RAM), read-only memory (ROM), electrically erasable programmable read-only memory (EEPROM), CD-ROM or other optical disk storage, smart cards, flash memory (e.g., card, stick, and solid state drive), magnetic cassettes, magnetic tapes, magnetic disk storage, magnetic strips, or other magnetic storage devices.

Retention of information such as computer-readable or computer-executable instructions, data structures, program modules, and the like, can also be accomplished by using any of a variety of the aforementioned communication media (as opposed to computer storage media) to encode one or more modulated data signals or carrier waves, or other transport mechanisms or communications protocols, and can include any wired or wireless information delivery mechanism. Note that the terms "modulated data signal" or "carrier wave" generally refer to a signal that has one or more of its characteristics set or changed in such a manner as to encode information in the signal. For example, communication media can include wired media such as a wired network or direct-wired connection carrying one or more modulated data signals, and wireless media such as acoustic, radio frequency (RF), infrared, laser, and other wireless media for transmitting and/or receiving one or more modulated data signals or carrier waves.

Furthermore, software, programs, and/or computer program products embodying some or all of the various wearable device implementations described herein, or portions thereof, may be stored, received, transmitted, or read from any desired combination of computer-readable or machine-readable media or storage devices and communication media in the form of computer-executable instructions or other data structures. Additionally, the claimed subject matter may be implemented as a method, apparatus, or article of manufacture using standard programming and/or engineering techniques to produce software, firmware, hardware, or any combination thereof to control a computer to implement the disclosed subject matter. The term "article of manufacture" as used herein is intended to encompass a computer program accessible from any computer-readable device, or media.

The device implementations described herein may be further described in the general context of computer-executable instructions, such as program modules, being executed by a computing device. Generally, program modules include routines, programs, objects, components, data structures, and the like, that perform particular tasks or implement particular abstract data types. The wearable device implementations may also be practiced in distributed computing environments where tasks are performed by one or more remote processing devices, or within a cloud of one or more devices, that are linked through one or more communications networks. In a distributed computing environment, program modules may be located in both local and remote computer storage media including media storage devices. Additionally, the aforementioned instructions may be implemented, in part or in whole, as hardware logic circuits, which may or may not include a processor.

Alternatively, or in addition, the functionality described herein can be performed, at least in part, by one or more hardware logic components. For example, and without limitation, illustrative types of hardware logic components that can be used include FPGAs, application-specific integrated circuits (ASICs), application-specific standard products (ASSPs), system-on-a-chip systems (SOCs), complex programmable logic devices (CPLDs), and so on.

Figure 5:
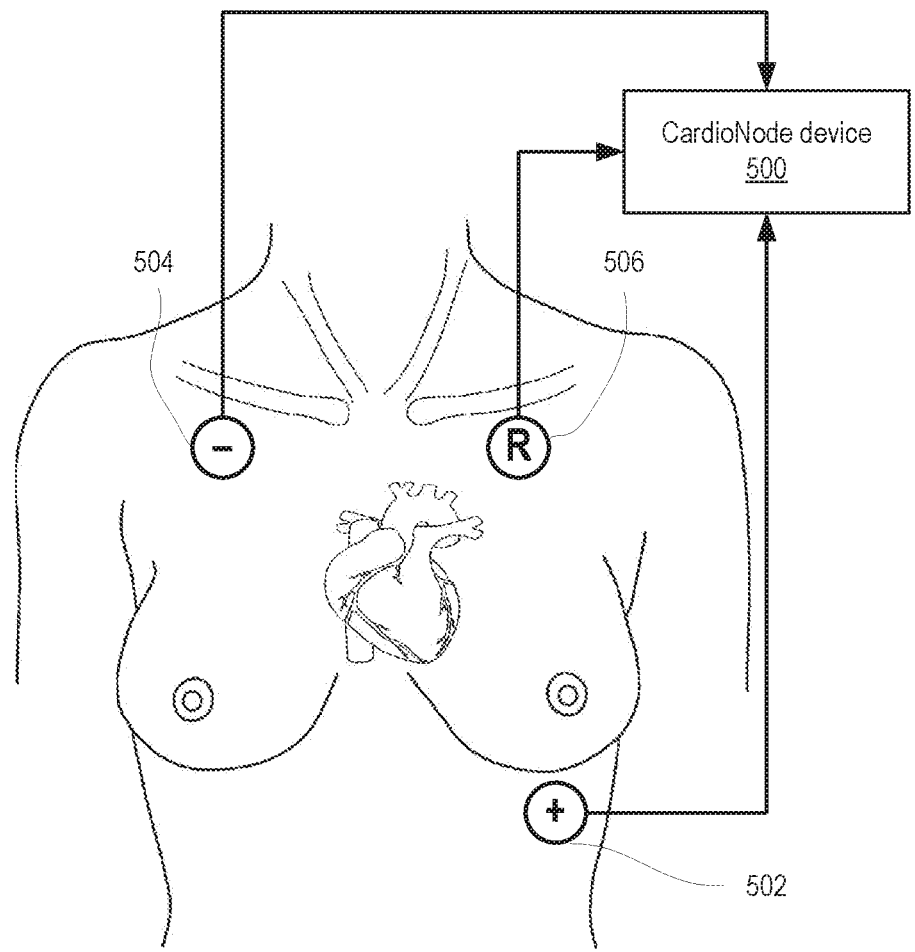
FIG. 5 is a front view illustrating a NeuroNode interfaced to detached nodes placed on a torso of user, according to one or more embodiments.

FIG. 5 illustrates a NeuroNode 500 interfaced to detached nodes: (i) first active electrode 502, second active electrode 504, and reference "R" electrode 506.

Figure 6:
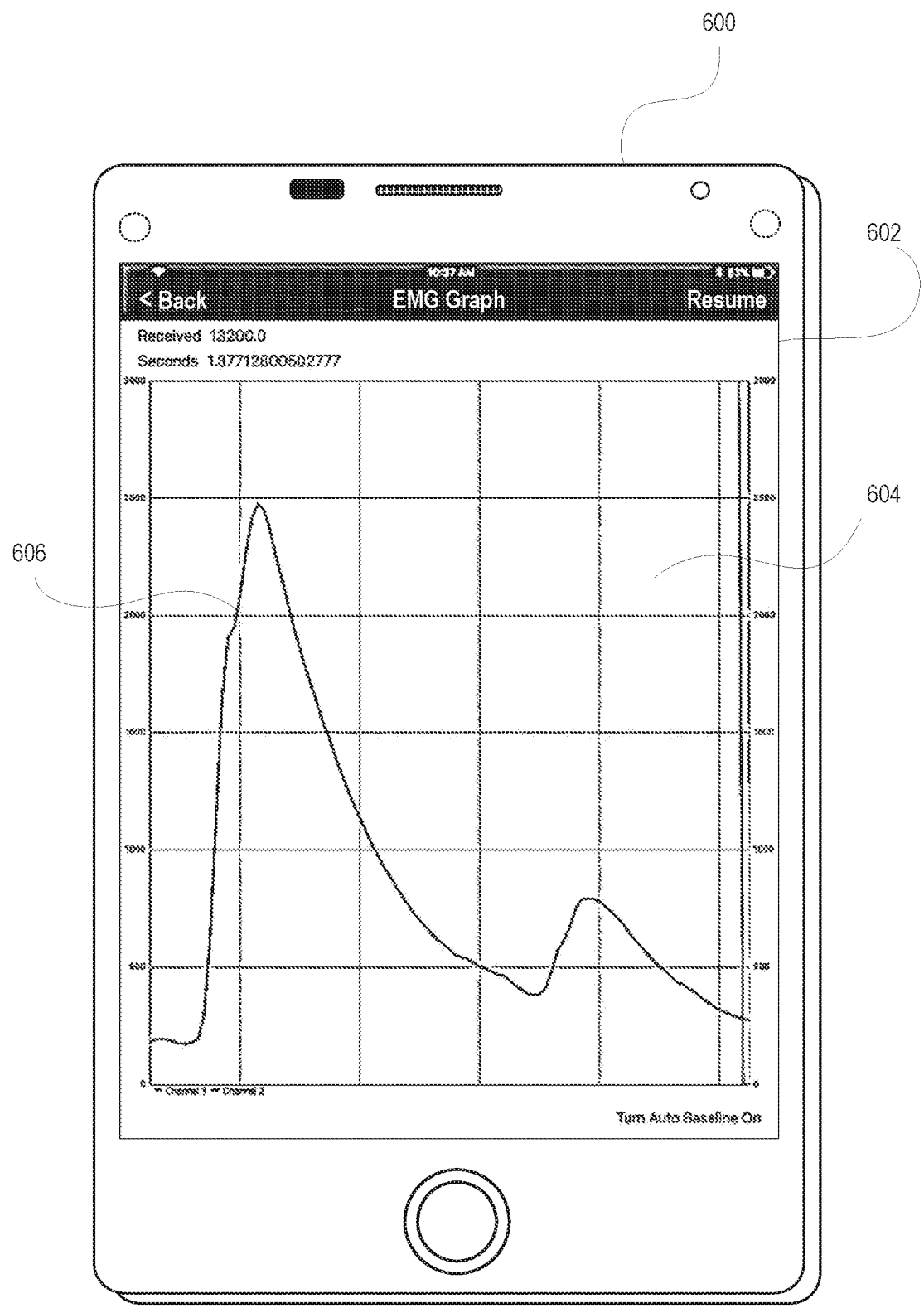
FIG. 6 is a front view illustrating a user device 600 having a user interface device that is presenting an electromyography (EMG) trace, according to one or more embodiments.

FIG. 6 illustrates a user device 600 having a user interface device, such as a touchscreen 602, that executes a physiological graph application 604. In this instance, the user interface device is presenting an EMG trace 606.

In some embodiments, the subject is partially or completely disabled, such as for example a quadriplegic subject, and the apparatus provides for control of a user device that facilitates control of a disabled subject's environment so that the subject can be at least partially self-sufficient. For example, in some embodiments the user device is a personal computer, a wheelchair, a bed, a telephone, a home appliance, and/or a speech synthesizer. Exemplary user devices can include or be a mobile phone, a smartphone, a PDA, a computer, and a media player. A media player can include or be any device suitable for displaying images, and/or playing sounds and/or video. In some embodiments, the subject is in need of controlling a complex user device or is functioning in a difficult environment and can utilize the assistive device to control the user device or function in the environment. For example, the subject in some embodiments can be a pilot, driver, scuba diver, or soldier.

Figure 7:
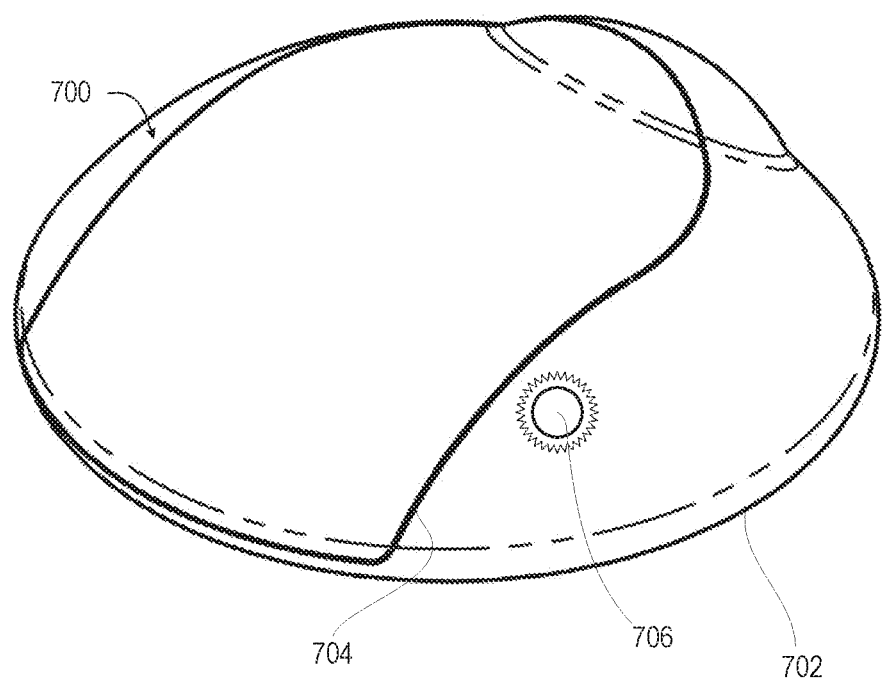
FIG. 7 is an isometric view illustrating an example NeuroNode device having an outer housing with a battery, according to one or more embodiments.
Figure 8:
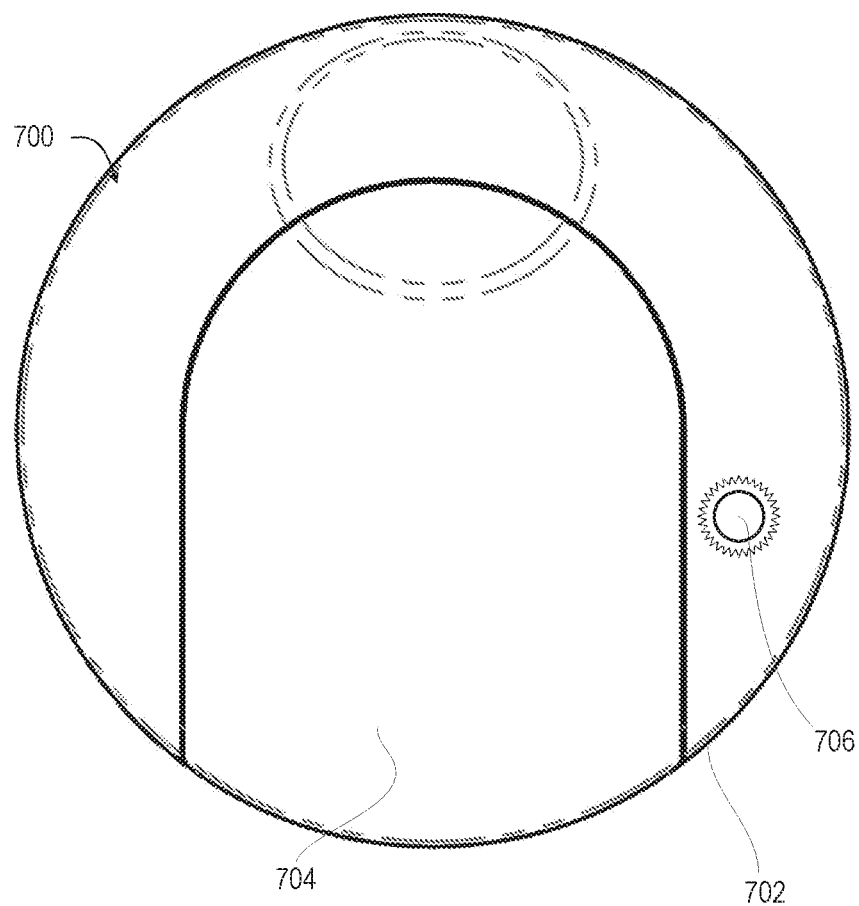
FIG. 8 is a top view of the example NeuroNode device having the outer housing with the battery, according to one or more embodiments.
Figure 9:
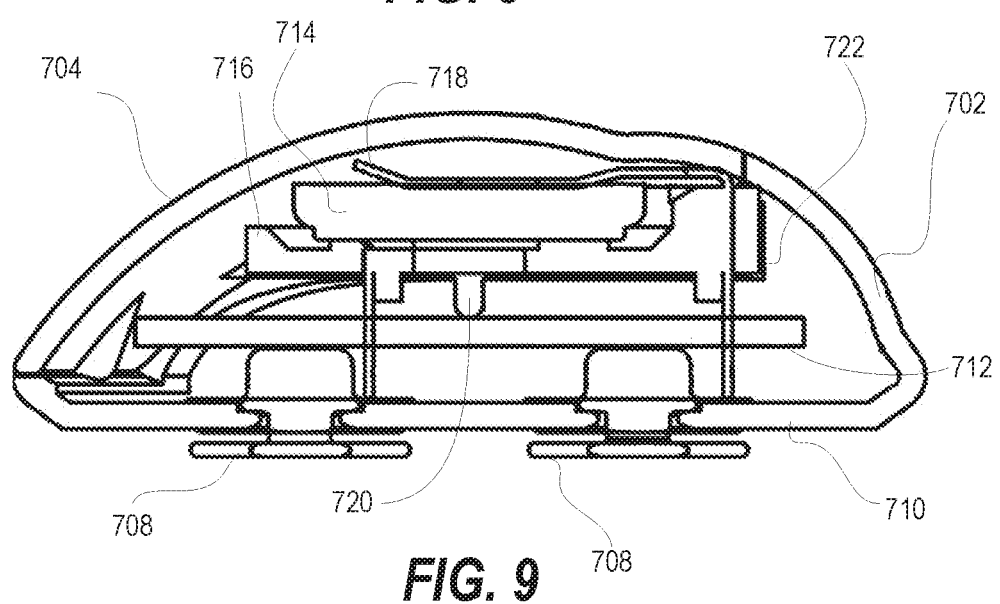
FIG. 9 is a side cutaway view illustrating the example NeuroNode device having the outer housing with a battery compartment, according to one or more embodiments.

FIGS. 7-8 illustrates an example NeuroNode device 700 having an outer housing 702 with a removable battery door 704. One or more light emitting diode (LED) indicators 706 can indicate various colors to communicate status and operating mode. FIG. 9 illustrates that electrodes 708 are snap fit inserted into an underside 710 of the outer housing 702. Each electrode 708 makes physical and electrical contact with a bottom surface of a printed circuit board (PCB) 712. A coin cell battery 714 beneath the battery door 704 is held in a battery receptacle 716 by a by a battery arm 718. A battery contact 720 extends from the battery receptacle 716 to the PCB 712 to provide an electrical ground. A battery contact 722 extends from the battery arm 718 to the PCB 712 to provide positive electrical voltage to power the NeuroNode device 700.

The NeuroNode device 700 can operate as a stand-alone EMG switch, capable of pairing with a variety of devices. If using the NeuroNode device 700 with an iOS device, the sensitivity can be set within NeuroNode controller application executed on the iOS device as described below. As a standalone switch, the NeuroNode device 700 has built-in indicators 706 in order to visually cue the user at the instance of a switch. A green indicator light indicates an EMG signal was counted as a switch. A blinking red light indicates that the NeuroNode device 700 is Bluetooth broadcasting. Upon powering up, the NeuroNode device 700 will go through a launch sequence as a series of colors such as green, blue, red and white. After passing through the launch sequence, the NeuroNode device 700 will remain on a solid color for a few seconds indicating a static threshold level: 10, 20, 50, 100, or 200 microvolts, or dynamic scaling. It is recognized that various color schemes may be used depending upon the application of the device.

Figure 10:
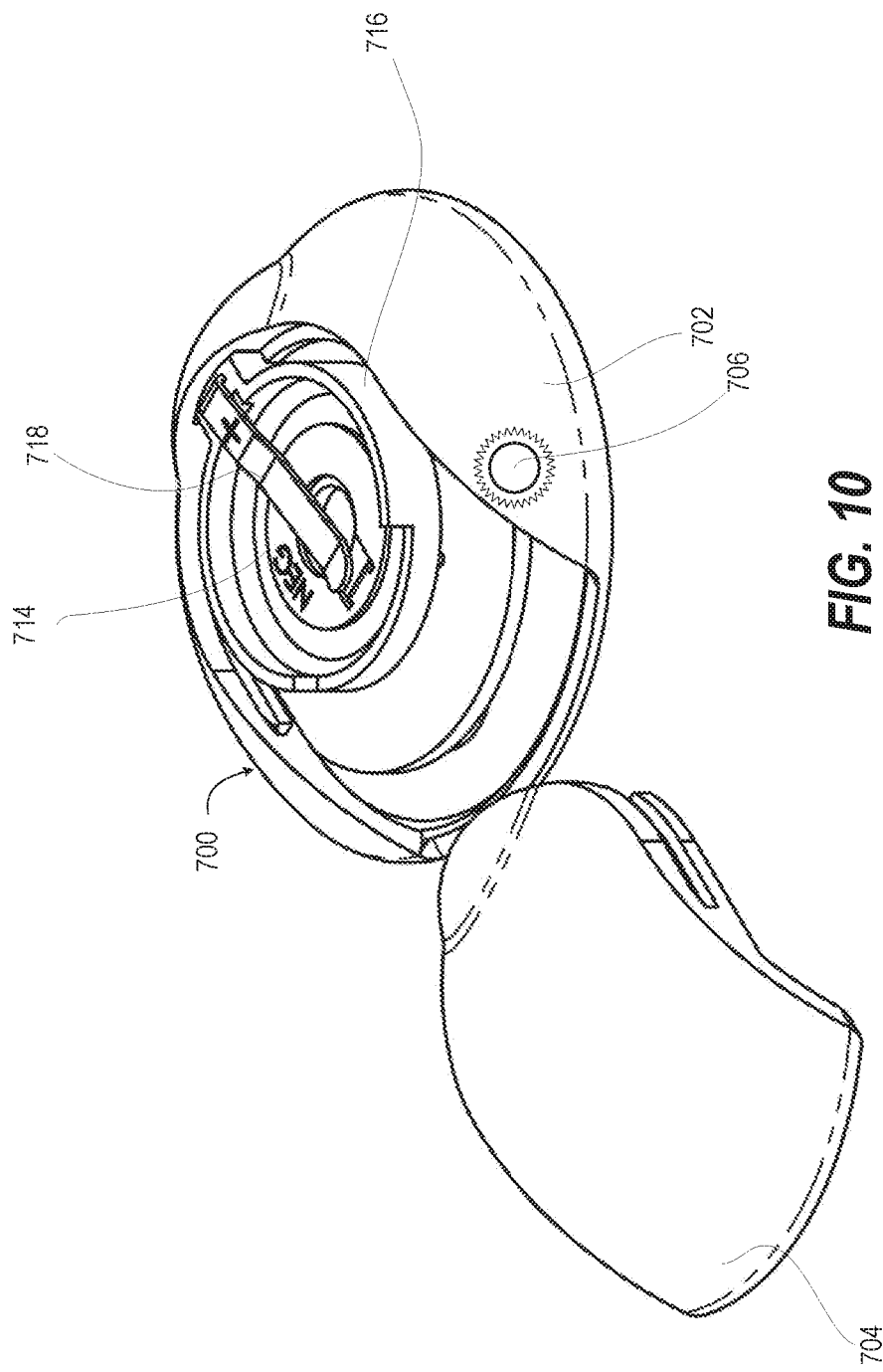
FIG. 10 is an isometric view illustrating the NeuroNode device with the battery door detached from the outer housing, according to one or more embodiments.

FIG. 10 illustrates the NeuroNode device 700 with the battery door 704 detached from the outer housing 702, exposing the coin battery 714 received in a battery receptacle 716, retained by the first active electrode arm 718. In one or more exemplary embodiments, the NeuroNode device 700 contains a battery 714 that is non-replaceable by the user.

In one or more exemplary embodiments, manually changing the threshold can be made by: (i) ensuring that the device Bluetooth is "OFF"; (ii) Power on the NeuroNode device 700 by inserting the battery 714 or performing a power cycle with a provided plastic collar stay or shim that is momentarily inserted between the battery 714 and the first active electrode 718; (iii) Upon performing the power cycle on the NeuroNode device 700, the NeuroNode device 700 will go through a launch sequence as the series of colors as previously described; (iv) Insert a pushpin tool to cycle through the threshold colors until the desired threshold is reached; (v) Attach the NeuroNode device 700 to the electrodes; (vi) Attach the electrodes to the user's skin; (vii) Test the user's signaling ability using the signal indicator 706. If the signal indicator 706 is always green, set the threshold to a higher scale. If the signal indicator 706 never turns green, set the threshold to a lower scale; (viii) Turn on the Bluetooth functionality of the NeuroNode device 700.

Figure 11:
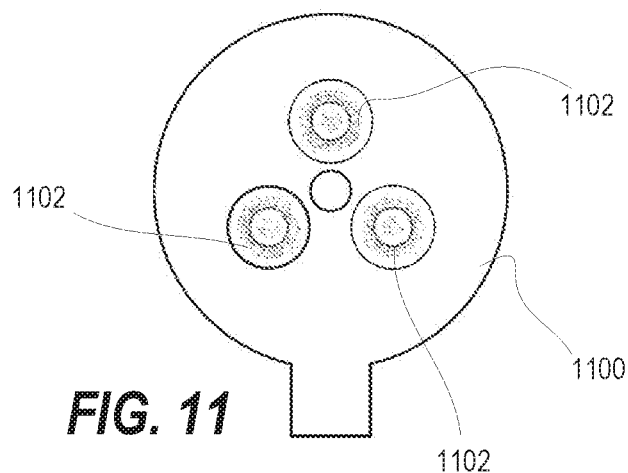
FIG. 11 is a top view illustrating a single adhesive disk with three (3) snap connectors that can be conveniently attached directly to the NeuroNode device, according to one or more embodiments.
Figure 12:
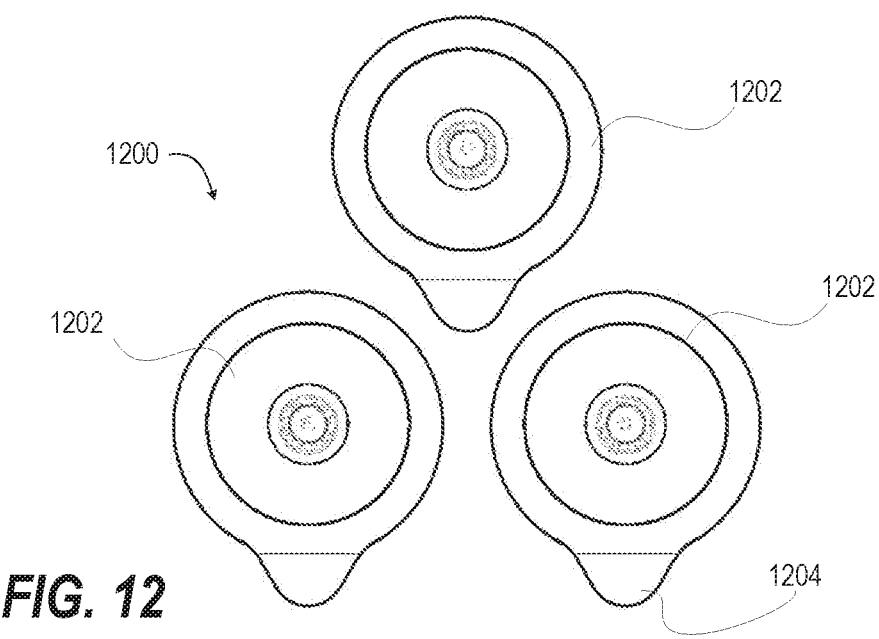
FIG. 12 is a top view illustrating an example of a set of three (3) individually gelled electrodes with a peel away tab for a reliable EMG signal acquisition and transmission, according to one or more embodiments.
Figure 13:
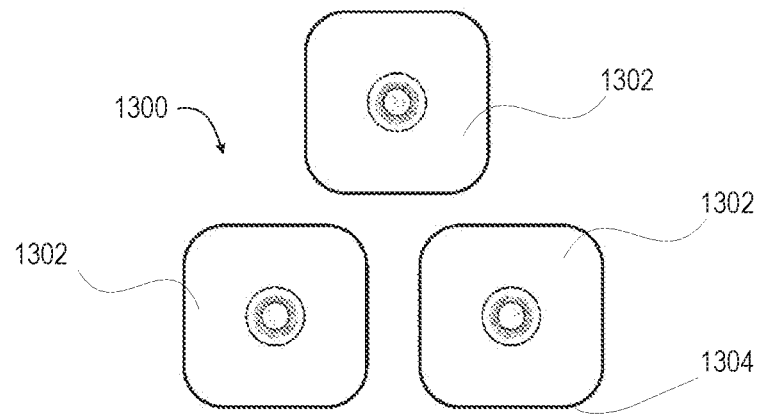
FIG. 13 is a top view illustrating an example of a set of three (3) individually gelled electrodes on a reduced size substrate, according to one or more embodiments.

FIG. 11 illustrates a single adhesive disk 1100 with three (3) snap connectors 1102 that can be conveniently attached directly to the NeuroNode device 700 (FIG. 9). FIG. 12 illustrates an example of a set 1200 of three (3) individually gelled electrodes 1202 with a peel away tab 1204 for a reliable EMG signal. FIG. 13 illustrates an example of a set 1300 of three (3) individually gelled electrodes 1302 on a reduced size substrate 1304. The individually gelled electrodes 1202, 1302 (FIGS. 12-13, respectively) can be connected to a lead wire adapter base that mounts to the NeuroNode device 700. Orient the plastic keying points on the face of the adapter plate with the matching keying points on the bottom of the NeuroNode device 700 (FIG. 9). Take care that the two pieces are aligned before snapping them together. Observe the black and white color-coding of the leadwires (two white, one black) and match them to the accompanying connectors exiting the adapter plate.

Figure 14:
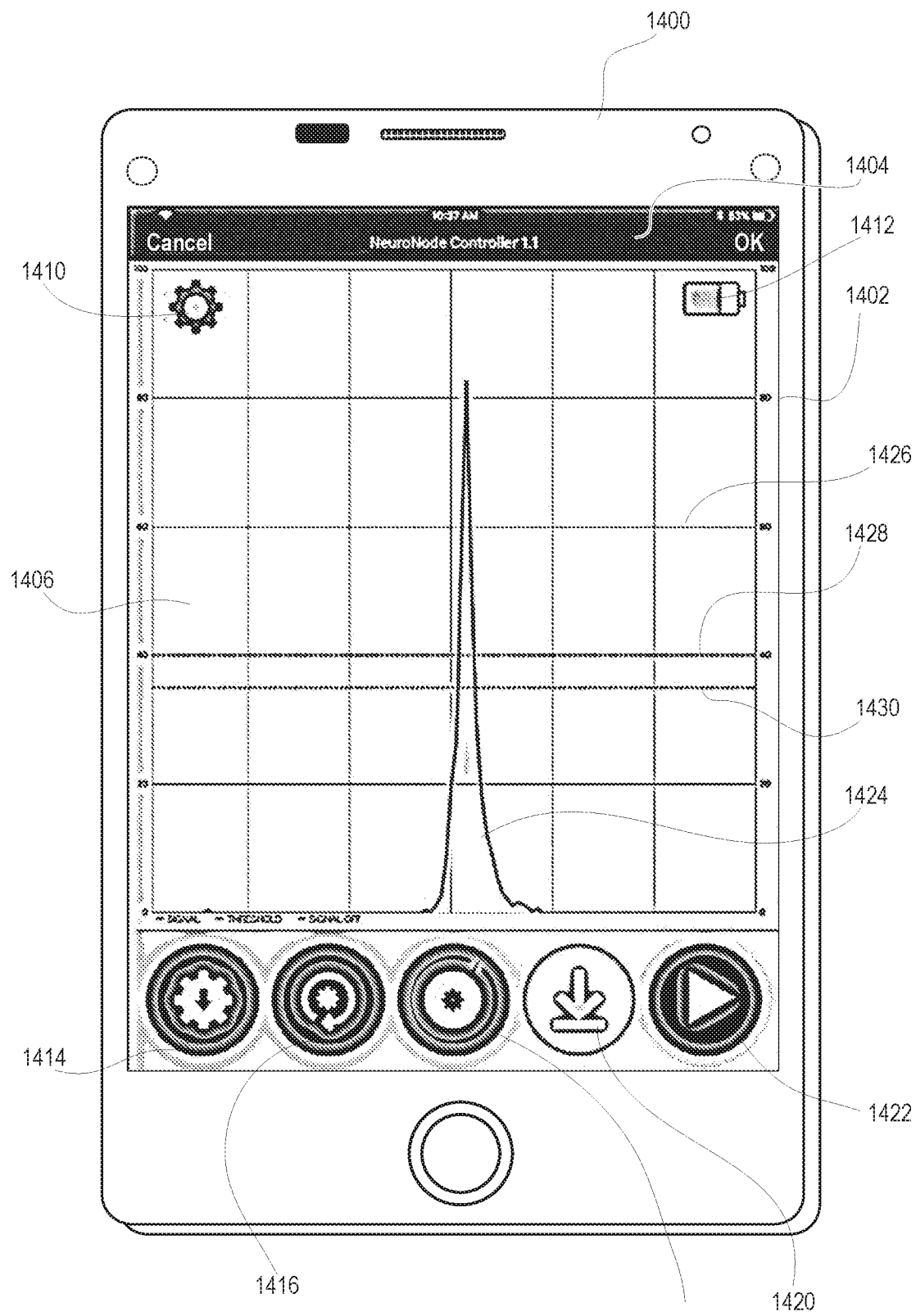
FIG. 14 is a front view illustrating a user device such as an iOS device having a user interface on which is presented a NeuroNode controller application, according to one or more embodiments.

In one or more exemplary embodiments, FIG. 14 illustrates a user device such as an iOS device 1400 having a user interface 1402 on which is presented a NeuroNode controller application 1404. The NeuroNode controller application 1404 performs as an EMG Augmented Assistive Communications (AAC) controller application that is designed to pair with the NeuroNode device 700 (FIG. 7) as an assistive control device. The application 1400 allows the user to adjust parameters and monitor EMG signal activity to ensure optimal signal outcomes that provide efficient and effective control of an iOS device 1400 utilizing Apple's accessibility suite. The NeuroNode controller application 1404, installed on the user's chosen iOS device, is used to set the signaling threshold while continuously graphing the EMG data stream. This smart application 1404 automatically re-calibrates to adjust to the user's strength and energy level without assistance from a caregiver or clinician.

The user interface 1402 presents a graph screen 1406 on which are provided: (i) NeuroNode controller settings icon 1410; (ii) NeuroNode battery level indicator 1412, (iii) save settings icon 1414; (iv) restore settings icon 1416; (v) edit graph settings icon 1418; (vi) reset resting level icon 1420; and (vii) pause/play icon 1422. A graphical depiction of EMG amplitude signal trace 1424 as a function of time is annotated with grid lines 1426, a threshold level indicator line 1428, and a signal off level indicator line 1430.

The save settings icon 1414 provides a user control to direct the NeuroNode controller application 1404 to store the current switching parameters in non-volatile memory of the NeuroNode device 700. On power-up, the NeuroNode controller application 1404 will load these saved settings to be used as the working switching parameters. The restore settings icon 1416 sets the application 1404 and the NeuroNode working switching parameters to the parameters read from the NeuroNode device 700 (FIG. 7) when the application 1404 was initially launched. Reset resting level icon 1420 sets a new baseline based on the user's current EMG resting level. The button is grayed-out if Auto Baseline is not turned on. Pause/play icon 1422 toggles the real-time EMG graph on (sweeping) and off (paused). Pausing the graph will put the NeuroNode device 700 (FIG. 7) in a low-power mode, nearly tripling its battery life. Also, when Paused, the NeuroNode device 700 (FIG. 7) will be disconnected as an input device. This can be helpful for performing maintenance or updates to the iOS device 1400 that requires the touchpad.

In one or more exemplary embodiments, Apple's Switch Control is integrated with the exemplary iOS device 1400, giving users and therapists versatile scanning technology to enter text, generate speech, and more. In one exemplary embodiment, the Apple iPad comprises Apple Switch Control icons: (i) Keyboard; (ii) Pointer; (iii) App; (iv) Clock: (v) Menu Bar; (vi) System; (vii) Custom; and (viii) Location. The Apple iPad comes with Apple's Switch Control word prediction and text-to-speech software. With Switch Control, NeuroNode enables users to write and have their words spoken by a choice of voices. The prediction accuracy will increase as the software learns the words and phrases that are used most often. Switch Control features include:

self-learning word prediction, and history and sentence prediction, with a choice of an English, Spanish, French, German, Italian, Swedish, Norwegian, Danish or Dutch user interface.

Figure 15:
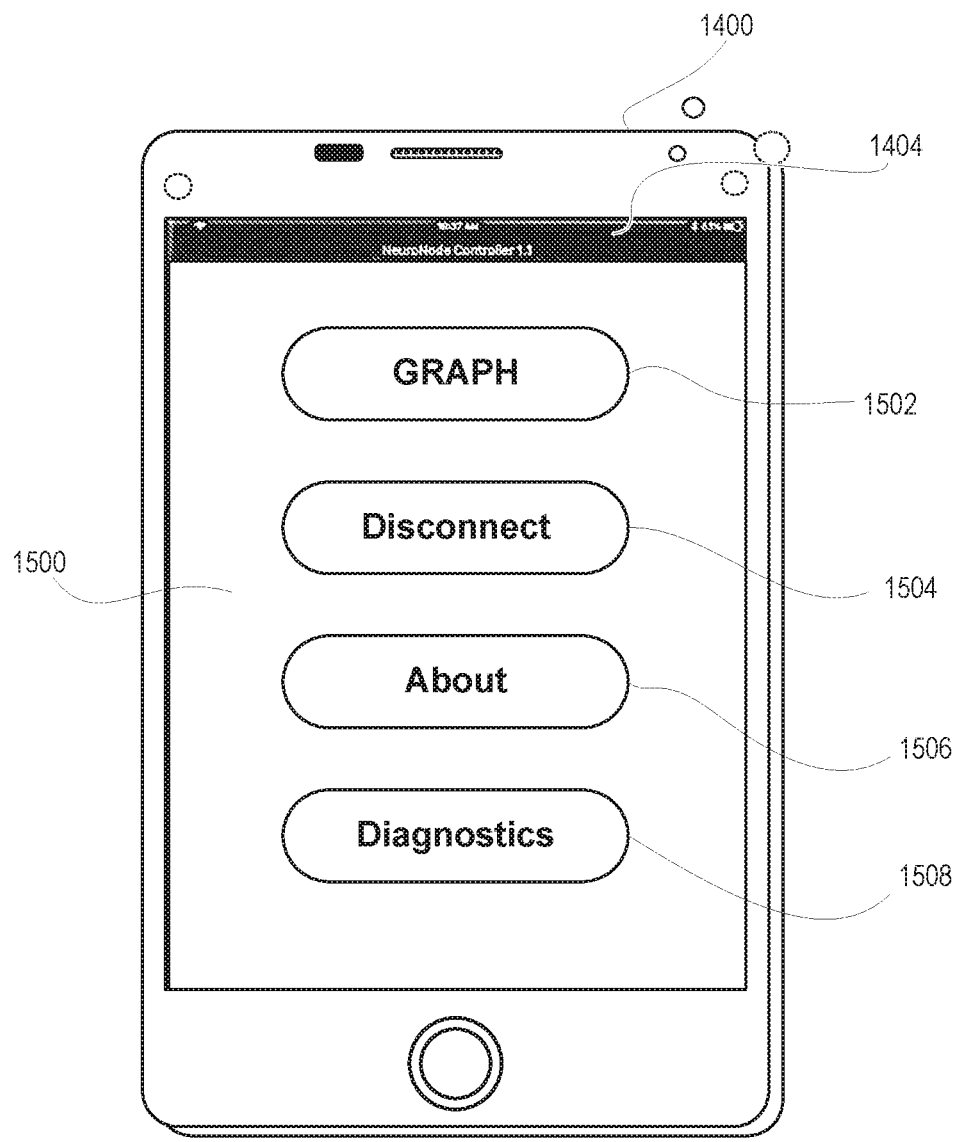
FIG. 15 is a front view illustrating the NeuroNode controller application in main menu mode, according to one or more embodiments.

FIG. 15 illustrates the NeuroNode controller application 1404 in main menu mode 1500 that includes a graph button 1502 that presents the graph display. A disconnect button 1504 disconnects the NeuroNode device 700 (FIG. 7). Touch on this button at times when the battery needs changed or when the NeuroNode device 700 (FIG. 7) will be out of use for more than 60 minutes. For shorter breaks in a session (and to conserve battery life), the user may temporarily pause the Graph Display to put the NeuroNode device 700 (FIG. 7) to sleep. The about button 1506 displays identifying information about this NeuroNode system, including the serial number of the NeuroNode, the software version of the Application, and the software version of the NeuroNode itself. Diagnostics button 1508 initiates self-test features.

Figure 16:
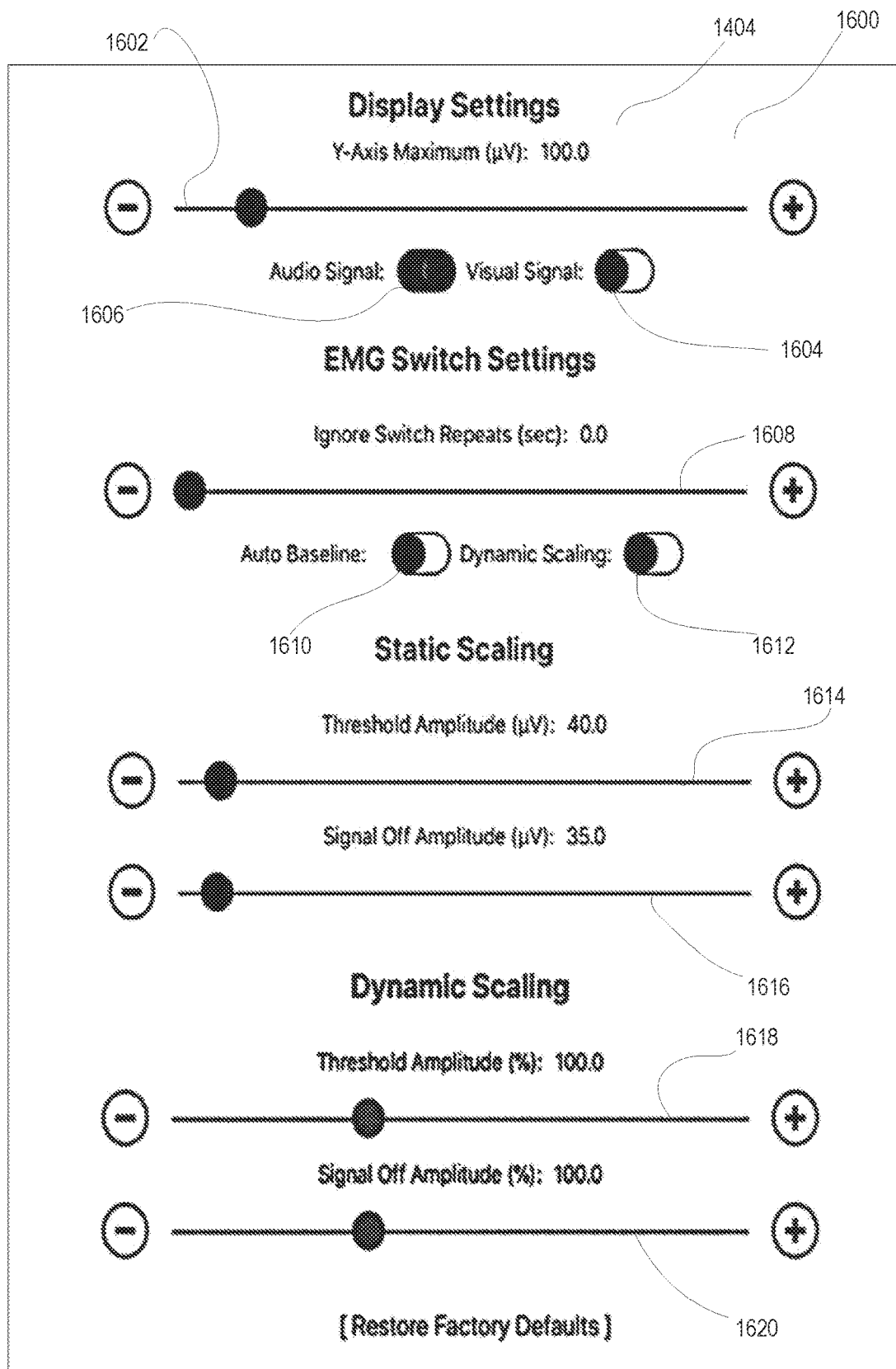
FIG. 16 is a front view illustrating the NeuroNode controller application in graph settings mode, according to one or more embodiments.

FIG. 16 illustrates the NeuroNode controller application 1404 in graph settings mode 1600 that is triggered by selecting the graph settings icon in the center of the applications icon dock. Y-axis maximum slider bar 1602 sets the full-scale range of the graph. Setting this parameter to 100 microvolts, for example, will allow EMG signals of 0 to 100 microvolts to fully appear on the graph. Visual signal indicator radio button 1604 directs the application to flash the display when a switch is made (i.e., when the signal crosses above the threshold amplitude.) Audio signal indicator radio button 1606 directs the application to beep when a switch is made (i.e., when the signal crosses above the threshold amplitude).

In one or more exemplary embodiments, an ignore switch repeats slider bar 1608 is helpful when the user is getting "false" switches after the original switch. These unintended switches can be the result of fasciculation or an inability to relax after making the original switch. Saving the ignore switch repeats setting to the NeuroNode can provide more consistent switching performance across multiple platforms and applications. Auto baseline indicator radio button 1610 sets the NeuroNode to a mode of operation where it will set a new baseline based on the user's current resting level. If the resting level decreases, the NeuroNode will use the resting level as the baseline. Dynamic/Static scaling radio button 1612 imposes respectively either a dynamic or a fixed criterion that the EMG signal must satisfy in order to be counted as a switch. The latter criteria remain unchanged over time.

When in static mode, the threshold amplitude slider bar 1614 sets the EMG amplitude that the signal must cross above in order to be counted as a switch. Signal off amplitude slider bar 1616 sets the EMG amplitude that a signal must fall before a new switch can be counted. Setting this parameter at the same level as the threshold amplitude will remove signal off amplitude as a switching determiner.

In one or more exemplary embodiments, dynamic scaling changes the criteria over time for determining if a switch has been made based on the user's performance. The EMG resting level and the EMG signaling level are both used in this ongoing calculation. As such, the NeuroNode will make it easier to switch as the user fatigues, or as the electrode interface conditions change.

When in dynamic mode, dynamic scaling threshold amplitude indicator slider bar 1618 sets a scale for use when in the NeuroNode's dynamic scaling mode. The lower the level, the more sensitive the NeuroNode will be in allowing a switch to be made. Signal off amplitude slider bar 1620 sets the level a switch must drop below before another switch is allowed. Setting this at 100% will set the signal off amplitude to the user's ongoing average resting level. Setting this parameter at the same level as the threshold amplitude will remove the signal off amplitude as a switching determiner.

In one or more exemplary embodiments, electrode placement entails choosing an EMG target muscle during the assessment, which can be changed at any point. Only one effective target muscle is needed to use the NeuroNode device 700 (FIG. 7). This muscle is chosen based on two criteria: (i) the muscle should respond, at least minimally, to a contract command; and (ii) the muscle should return to a resting state in a timely manner. The muscle does not need to function at optimal levels. The NeuroNode device 700 (FIG. 7) is designed to respond reliably and accurately to minimal signals at the target muscle site.

Although the placement of the NeuroNode does not have to be exact, there are some general guidelines for placing the device onto the target muscle site. When using a triple electrode (FIG. 11), the two active electrodes are located on the bottom of the NeuroNode, running parallel to the battery cover. When using single electrodes and leadwire adapter base (FIGS. 12 and 13), the two active electrodes (white snaps) should be placed along the length of the muscle, which is being used to generate a switch. The reference electrode (black snap) can be placed in an isosceles triangle relationship to the other two active electrodes or on some electrically neutral site on the body.

Upon establishing a good signal and before starting Switch Control, a good signal is established with the NeuroNode that will become the user's switch for selecting items on the assistive technology device. A good signal is characterized by having a clear delineation between a resting level and a switching level.

In one or more exemplary embodiments, Turning Switch Control on and off is performed by: Step 1: select the settings icon on the iOS device. Step 2: select the general tab within settings. Step 3: select the accessibility settings within the general tab. step 4: select Switch Control with the accessibility tab. A green Switch Control switch indicates that the Switch Control is on. Step 5: tap on the Switch Control switch to turn on Switch Control. A gray Switch Control switch indicates that Switch Control is off.

In one or more exemplary embodiments, Switch Control can be configured with multiple switches. For the NeuroNode, one of the switch actions can be to choose the selected item.

In one or more exemplary embodiments, Scanning style can be configured with autoscanning selection, which moves the focus while scanning after a set duration. In one or more embodiments, manual scanning selection requires a switch to be made in order to move focus, and another switch to be made in order to select an item. Single switch scanning selection requires a switch to be made in order to move focus. If no action is taken after a set duration, the item with focus is automatically selected.

Auto scanning time is the number of seconds (for example, up to 5, 10, 15, 20, 25, 30 seconds or more) that are required to step from one item to another in a panel when using autoscanning style. Pause on first item selection is the number of seconds (for example, up to 2, 3, 4, 5, 6, 7, 8, 9, 10 seconds or more) that autoscanning stays on the first item in panel, group or user interface. Loops setting sets the number of times Switch Control repeats a scan. Tap behavior setting adjusts what happens when a switch activated to select an item. Default setting shows the scanner menu upon selecting an item. Auto tap setting automatically selects the item unless another switch is made during the set duration, at which time the scanner menu will appear. Always tap setting automatically select the highlighted item instead of showing the scanner menu. This setting only works while scanning in item mode and puts the scanner menu at the end of the scan. Focused item after tap setting determines where the scan restarts after an item is selected, either the "first item" (i.e., the beginning of the scan) or at the "current item." Ignore repeat setting is the number of seconds (for example, up to 6, 7, 8, 9, 10, 12, 14, 16 seconds or more) during which repeated pressing of a switch is ignored. Gliding cursor speed is the speed from "1" (slow) to "100" (fast) at which the gliding cursor moves across the screen. Use this setting to adjust the speed while in point mode. Speech setting turns on or off audio cues during scanning. Cursor color setting controls the color of the gliding cursor in point mode or the color of the grouped items in item mode.

Setting an accessibility shortcut provides a quick, efficient way to turn Switch Control on and off without entering the system settings. In order to create an accessibility shortcut, the accessibility settings are configured by enabling Switch Control as previously described. Then the accessibility shortcut setting is set to "Switch Control", allowing the user to turn Switch Control on and off by pressing the home button on and off three times in quick succession.

In one or more exemplary embodiments, guided access setting limits an iOS device to a single application and allows the user to control which application features are available. With guided access, the user is able to temporarily restrict an iOS device to a single application and, more importantly, to disable areas of the screen where an accidental gesture or selection may cause an unwanted action.

In one exemplary mode, from the iOS device home screen, the default Switch Control scanning mode is item mode. Item mode highlights items or groups on the screen one at a time. Point mode allows selection of an item on the screen by pinpointing it with scanning crosshairs. Changing from point mode to item mode includes adjusting the timing parameters within Switch Control tap behavior settings. Step 1: The default setting is auto tap set to 0.20 seconds that should be adjusted to 2.0 seconds. Step 2: scan to and select any item on the iOS device. Once an item is selected, make another switch with 2 seconds to display the scanner menu. Step 3: scan to and select item mode. If in item mode, scan to and select point mode. In order to increase overall speed, it may be helpful to return to Switch Control tap behavior.

The NeuroNode will also work with eye tracking devices (also referred to as eye gaze). Eye tracking is a technology that tracks the motion of the eye relative to the head. In a normal embodiment, the eye tracker will determine the user's intention by observing where the eyes are trained and then processing a 'Selection'. A Selection is the process of choosing what the eyes are trained on. Normally, a selection is made by maintaining the gaze in position for some predetermined time or by performing an eye closure. The NeuroNode system can be used as the Selection mechanism as a replacement for standard Selection strategies. The NeuroNode for Selection can significantly increase the speed of eye tracking communication while significantly decreasing the user fatigue associated with other Selection methods.

It should be understood that the invention's eye gaze user interface and method can be implemented on a wide variety of different types of eye gaze detection and virtual display devices, some head mounted, and some not. In some cases, the device may be head mounted, and in other case the device may not be head mounted. Some devices may only monitor the gaze direction of one of the user's eyes, while other devices may monitor the gaze direction of both of the user's eyes. The device will generally have a display upon which various visual targets, such as symbols, may be displayed in order to give the user something specific to gaze at. Although in this specification, generally such displays are shown as see-through virtual displays (because this type of display enables a user to see the surroundings beyond the virtual display), in some embodiments the device utilize a standard, non-see-through, type display The device may monitor eye gaze directions by many methods, including video cameras trained on the eye along with automated image analysis software that interprets eye gaze direction from the visual appearance of the eye. Alternately the device may monitor eye gaze direction by bouncing light off of the surface of the eye and noting the direction of the reflected beam or beams of light, or other means.

The device will typically be a computer operated device, often including at least one microprocessor, memory, and software to control the visual display. The device will generally take input from the eye gaze sensor or sensors and convert this input into an eye gaze direction, as well as correlate this eye gaze direction with a particular visible element and eye position zone associated with this particular visible element on the devices' display. The device may additionally contain communications devices, such as wired or wireless network connections to communicate to and from other outside devices, cell phone networks, and networks such as the Internet. Note that although in some embodiments, this microprocessor and communications devices may be internal to a device that in turn is mounted on the user's head, in other embodiments, the device may be more of a dumb device, and microprocessor(s) and communications devices may instead be outside of the device, and in some cases connected to the device by a cable.

Contextual Embodiments

The present disclosure illustrates various techniques and configurations to enable a series of dynamic workflows for the selection and presentation of content from an information system relevant to activities of a human user. The dynamic workflows used with the NeuroNode as described herein enable the integration of user interfaces and user communication platforms to achieve relevant and timely communication among users and others and related actions. The dynamic workflows described herein further may be integrated with social networks and portable communication mediums, to provide additional availability and delivery of content to users in a variety of settings.

In one example, an internet-hosted information service is offered to users through a series of dynamically changing user interfaces. For example, a software application may be used to collect, display, and deliver relevant and timely communication, suggestions, and content to and from a user. The information service may be used to directly interact and implement aspects of a workflow with a subject human user or patient, while also facilitating interaction with other humans or agents, such as friends, family, experts, professionals, and the like.

The workflows may integrate with various evaluations that dynamically assess a user's current state. For example, user interaction from a series of evaluations may be collected to monitor and measure a user's health, location, time and date, other persons nearby, etc., to facilitate real-time, interaction with the user.

The dynamic workflows and the various interaction applications of the NeuroNode as described by the present disclosure may be configured for receipt, processing, and delivery of relevant content from an electronic information system. The information system, as further described herein, may implement human interaction with a series of workflows and processing activities that deliver relevant content to encourage human activity and progress towards an ultimate goal. Relevant content may be provided in a push or pull manner, on schedule or in response to determined conditions, and manually or automatically from the information system, in accordance with the following techniques.

In one or more embodiments, the experience for a user of a computing device of the present invention may be significantly enhanced by operating the computing device in a way that is context dependent. The context, and hence a desired operation of the computing device, may be determined based on the location of the computing device and actions from which intent of the user may be inferred. Such operation may be achieved with a computing device that can sense its position relative to locations that have been designated as being associated with a desired configuration of the computing device. For example, a computing device whose location is in a bedroom may automatically configure itself as an alarm clock or bring up menus for sleep/wake activities. In some embodiments, the context of a computing device may be determined by reading values from tags using a proximity-based radio. The tags may be passive tags, responding the radiation emitted by the computing device.

A context-sensitive user interface input may be provided. Consistent with embodiments of the present invention, a user interface element comprising text input may be provided as part of an application user interface (UI). The UI element may comprise graphical assistance presented to a user as they type to aid in building an application action. The UI element may provide context-sensitive suggestions; that is, given what the element knows about the user's context (e.g. an application focus such as a calendar or an email function and what the user has typed already), the control may offer different options and/or suggestions as to what the user may enter next.

Disclosed are an example system and example methods for retrieving content based on context in a mobile environment. In one example embodiment, the method includes using an application in the NeuroNode system 100 (FIG. 1) that receives events when a user is interacting with a specified application in the device. During operation, the application starts monitoring a specified application for context information. When the application detects the existence of context information, it may retrieve the context information from the specified application and use the retrieved context information to search content of other applications in the device that is related to the retrieved context information.

The user interface control may comprise a text-box in which the user may type actions. Actions may comprise "sentences" that may follow a grammar defined by the application. As the user enters "token" (words) and builds the action, a graphical user interface may follow the text caret and may provide suggestions on tokens that may be typed next and/or selected to continue to build the action. Once the user is done, a completed executable action may be sent to the application for processing.

The contextual application may monitor other applications installed on device for context information at a predetermined context. In some example embodiments, the predetermined context may be a specific application or applications. In other example embodiments, the predetermined context may refer to a specific field or fields within one or more applications. In still other example embodiments, the predetermined context may be a specified graphical interface screen or screen (i.e., page or pages) within one or more application. In yet other example embodiments, the predetermined context may be certain information or data automatically provided by a system service, such as a location from a global positioning system service; a date from a calendar service; or a time from a clock service, of the device.

Contextual information can be used for a wide variety of applications and can generally be characterized as information that is relevant to an understanding of something. For example, traditionally, context includes information about a location and its surrounding environment, the identity of things named in a text such as people, places, books, and so on. However, other types of information promise to be of as much or even greater benefit for next-generation communication services Using context information, an application may search and provide results from other applications that are relevant to the context information. The application may receive contextual information when the user of the device is interacting with one or more specified applications, and retrieve content from the application being accessed when such application meets a set of criteria or predetermined context.

In other example embodiments, the contextual application may be configured to notify the user of the device of the results in one or more unobtrusive methods. For example, the retrieved content may be displayed in a status bar or notifications bar of the NeuroNode system, or in an indicator indicating that relevant content has been retrieved and may be displayed in a status window (such as where connectivity strength or battery life remaining are typically found). In another example embodiment, the contextual application may transmit the results or a notification that results have been received to a device located remotely from and communicatively coupled to the NeuroNode system. Such remote device may be a mobile device or a watch capable of communicating with the NeuroNode system via a wired or wireless connection such as Bluetooth or Wi-Fi. Such transmissions may be in addition to or in lieu of notifications within the NeuroNode system.

The contextual application may be any application or another computer program installed on the NeuroNode system which is executable by a processor and can be stored on a computer-readable media. In some example embodiments, the contextual application may refer to firmware and/or a combination of software and firmware. In some other example embodiments, the contextual application may be executed on the web or over a network. The contextual application may process, organize, manipulate, store, generate, display, and/or otherwise render context information that can be used by the contextual application to retrieve content from other applications.

In one or more embodiments, the contextual application may be configured to monitor all applications running on NeuroNode system. When a user interaction occurs for any application running on NeuroNode system, contextual application may be notified. Contextual application may then determine whether the application with which the interaction occurs is identified in a defined configuration. In some other example aspects, contextual application may be configured to monitor only specific applications such as, for example, Contacts application, for interaction by a user of NeuroNode system.

Contextual application may include one or more settings that allow a manufacturer, service provider and/or user of NeuroNode system to set which of the other applications installed on NeuroNode system will be monitored and to configure the predetermined context for the applications to be monitored. In some alternative example embodiments, a manufacturer, service provider and/or administrator of contextual application may configure the contextual settings and/or the predetermined context.

In one or more embodiments, the contextual application may be configured to monitor or detect applications for a particular event occurring in the NeuroNode system. An event may be any event performed as a result of user interaction with NeuroNode system, any event performed as a result of sensors such as RFID, GPS, facial recognition, voice recognisiton, time/date, etc. In some example embodiments, events may refer to events triggered by device sensors or system services, such as, for example, location services, accessibility helper services, or date and time services.

User interactions may refer to an event within the NeuroNode system wherein the user accesses certain applications such that a window of a contacts list application is displayed in the user interface of the NeuroNode system. Once context information is set and/or retrieved, the context information may be utilized by one or more contextual applications to retrieve content related to the context information from one or more applications.

In one example embodiment, contextual applications may run in the background while another application is being accessed such that when a user accesses and interacts with an application, the contextual application may retrieve the context information without user intervention and/or unobtrusively from an application and utilize the retrieved context information to search for content from any applications.

In some alternative example embodiments, applications may be installed on a device or devices communicatively coupled to NeuroNode system. For example, the applications may be web or other applications stored on a remote server or other mobile device, such as a tablet computer or a watch, and contextual application may search for data from applications via a wired or wireless connection, such as Bluetooth or Wi-Fi.

In one or more embodiments, the contextual application may be configured for use with users or patients having a temporary disability or condition that prevents the user from normal computer or mobile device interaction. For example, a person confined in a hospital bed can utilize the NeuroNode system to communicate, control devices, signal interactions or emergency events, etc. In some example embodiments, a person may not be suffering from a physical disability but may be constrained due to environmental or situational factors such a person confined on a subway or an airplane where the person could utilize the NeuroNode system to communicate, control devices, and otherwise interact electronically without having to resort to writing, gestures or vocalizations. An event may be any event performed as a result of user interaction with NeuroNode system, any event performed as a result of sensors such as RFID, GPS, facial recognition, voice recognition, time/date, etc. In some example embodiments, events may refer to events triggered by device sensors or system services, such as, for example, location services, accessibility helper services, or date and time services.

In one or more embodiments, the contextual application may be configured to monitor or detect applications for a particular event occurring without the NeuroNode system. An event may be any event performed as a result of user interaction with one or more sensors, any event performed as a result of sensors such as RFID, GPS, facial recognition, voice recognisiton, time/date, etc. In some example embodiments, events may refer to events triggered by device sensors or system services, such as, for example, location services, accessibility helper services, or date and time services.

In one or more embodiments, the contextual application may be configured for utilization of the context-sensitive user interface element where text input may be provided as part of an application user interface (UI) with or without the NeuroNode system. For example, a person may temporary or permanent mental disabilities such as a geriatric patient or people with Alzheimer's disease or dementia in general where the user can make use of the contextually-sensitive user interface element to present a hierarchical system of panels for a user experience that guides the patient or user through the course of the day. For example, the system gathers context about the user's environment and adjusts the communication options based on this context.

Further, it is understood that any number of panels may present information in a paged manner. By "paging" and as used herein, it is meant an approach for taking a large or substantial list of items and segmenting them such that in a network perspective, data and/or information may be presented in a quick and efficient manner. By incorporating paging in the display, any number of the panels will only transmit a portion of the data across the network, which in turn may reduce data transfer costs and reduce delays due to this data transfer. It will be understood that one example of paging is infinite scrolling, whereby presented information automatically pages subsequent segmented information upon scrolling to the end of the currently presented page.

Context for custom communication panels can be gathered through automatic queries to an AI device or through other sensor systems. Context could be time-of-day, persons in proximity of the user, temperature, day of the week, calendar entries, medical data or sensor input, or any other input that would change what the user may want to say or do. A communication panel appears for the user on his computer (device) offering these customized choices. This could be in the form of a list or an array of buttons and includes third-party context, which brings up certain pre-made panels of items depending on a person present (or mentioned). A context generated button appears for "How was school", for example, if it is 4:00 pm on a weekday and the school-age daughter walks into the room. Context generated button "Can you take me outside?" appears, for example, if the caregiver is in the room in the afternoon and the current weather is sunny with no chance of rain. The system can be used to control and operate smart appliances without having to remember the names and directions utilizing context-sensitive switching. Smart residential systems can include one or more residential appliances, such as, but not limited to, a refrigerator, stove, microwave, toaster, coffee-maker, alarm clock, thermostats, humidifiers, sprinkler system, lighting, light dimmers, etc. In one or more embodiment, control server and/or controller client controls the operations and/or functions of one or more residential appliances, such as on/off, timers, modulation (e.g., oven temperatures, etc.), pause, snooze, etc.

In one or more embodiments, the predetermined context may be a Hypertext Markup Language (HTML) tag or HTML user interface (UI) element, container, or variable that contains information, data or value that may be used by another application to locate a record. The HTML elements may be components of an HTML document and the information, data or value may include other HTML elements, text, and the like. The data in the configured field may be any data type capable of being recognized by an application such as, for example, a label, a string identifier, a number identifier, or any string of text.

In another example embodiment, the predetermined context may be an Extensible Markup Language (XML) tag or corresponding user interface (UI) element, container, or variable that contains information, data or value that may be used by another application to locate a record. The XML elements may be components of an XML document and the information, data or value may include other XML elements, text, and the like. The XML element may be referenced via an XML Path Language (XPath) location path. The data in the configured field may be any data type capable of being recognized by an application such as, for example, a label, a string identifier, a number identifier, or any string of text.

In some example aspects, such as where an application has multiple user interfaces or pages, a specific interface from where information can be retrieved may be set in the defined configuration of contextual application. In such example aspects, determining if the event meets the defined configuration may include verifying that the user interface or page currently being accessed by a user (i.e., the "active" interface or page) is the user interface of the application specifically defined as a predetermined context.

In some example aspects, contextual application may also provide a notification to the device user regarding the identification or availability of results of the search for content related to the context information. In some example embodiments, the providing of notification to the user may be performed in unobtrusive manner using a notification layer in NeuroNode system. In other example embodiments, the notifications may be message sent via text or e-mail. Other unobtrusive methods of providing notification to the user while the user is accessing application will be known in the art. In some alternative example embodiments, a mobile device, such as a smart watch, may be communicatively connected to NeuroNode system. In such example embodiments, notifications of search results may be sent to the second mobile device. Such notifications may occur through text or e-mail messages, vibrations, lights, background changes or other known methods.

In one or more embodiments, the present invention provide systems and methods for implementing an interaction model with the user in order to interact with data of any data source in a natural way. In some examples, the system receives natural language input from the user and processes the input using multiple technologies such as keyword mapping, fuzzy logic, context-sensitivity and historical search data.

In one or more embodiments, the present invention provide systems and methods for data retrieval using an interactive, dynamic model that enables a self-learning and context-sensitive semantic layer to allow a user to retrieve and report data in a natural way from one or more data sources. Instead of pushing the user into a pre-defined or static model thereby allowing the user access to only a pre-defined set of questions and data reporting, the system allows the user to explore data in a manner similar to a conversation, e.g., starting on a broad level and then detailing into specific areas that he/she is attempting to locate.

In one or more embodiments, the NeuroNode system is configured to learn on multiple levels as the user uses the system more. In one or more embodiments, if the NeuroNode system does not understand how a keyword is mapped to an existing data structure (e.g., how it is mapped to a data entry or table name of the data sources), the NeuroNode system provides an interactive object that receives information about the keyword from the user.

In one or more embodiments, one or more context-sensitive main communication panel modules are disclosed that are configured connect one or more front-end systems, such as one or more digital assistants, to one or more back-end systems that are deployed in a user environment. A digital assistant, also referred to as a virtual assistant or chatbot, is a software agent that is configurable to perform tasks for a user. Examples of digital assistants include Apple Siri, Google Assistant, Amazon Alexa, and Microsoft Cortana. Digital assistants typically interact with users via one or more of text (e.g., online chat, such an instant message application), voice, image, or video inputs or outputs. Digital assistants use natural language processing (NLP) to match user inputs to user intents. Many digital assistants use artificial intelligence techniques, including machine learning, to improve their matching performance. Digital assistants are typically activated using a wake word (e.g., "Alexa" for Amazon ALEXA or "OK Google" for Google ASSISTANT).

In one or more embodiments, the one or more one or more context-sensitive main communication panel modules include a module that is configured to infer at least one of an intent, context, or classification from a command received at the one or more front-end systems, a learning module that is configured to generate one or more requests (e.g., distribute one or more commands to the one or more back-end systems), receive one or more responses to the one or more requests, format the responses according to one or more machine-learned presentation rules, and generate insights for use in future command processing, and a looking module that is configured to generate the one or more responses to the one or more requests (e.g., by executing the one or more commands, such as commands for querying or scraping data sources associated with the back-end system and/or data sources external to the one or more back-end systems, such as external public data sources). In one or more embodiments, the output of the responses is through one or more connected front-end systems, such as one or more digital assistants.

In example embodiments, learning modules employ machine-learning techniques to learn workflows associated with each user environment, including user-specific vocabularies that are used for purposes of determining intent, context, and classification of command received from the front-end systems, and mapping of commands received from the one or more front-end systems to the machine-learned user workflows. Based on a machined-learned mapping of the query to a machine-learned pathway into one or more of the back-end systems deployed, as discussed above, the learning module automatically submits one or more requests to one or more back-end systems deployed on behalf of the user.

Figure 17:
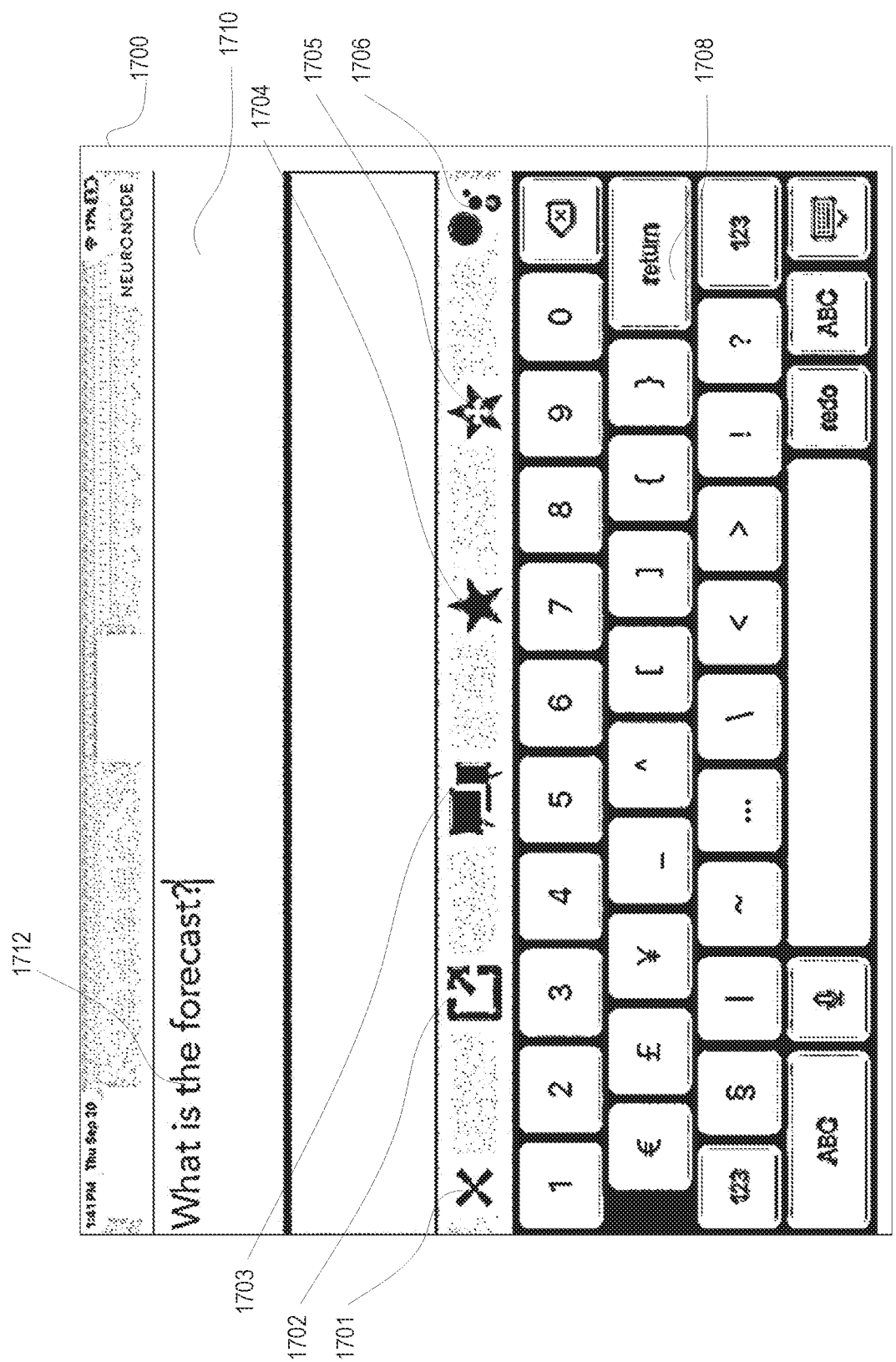
FIG. 17 is a screen depiction illustrating a context-sensitive main communication panel as an artificial intelligence (AI) interface to the NeuroNode system, according to one or more embodiments.

FIG. 17 is a screen depiction illustrating a context-sensitive main communication panel 1700 as an artificial intelligence (AI) interface to the NeuroNode system 100 (FIG. 1). Main communication panel 1700 includes menu icons 1701-1706, an alphanumeric keypad 1708, and a query entry box 1710. Menu icons 1701-1706 can include delete icon 1701, send to NeuroNode system icon 1702, text-to-speech session icon 1703, access favorites icon 1704, save AI query to Favorites icon 1705, and send query directly to AI device icon 1706. The main communication panel enables a speech-impaired and/or mobility-impaired user to use an AI device such as GOOGLE ASSISTANT without speech and with a minimum of muscular control. User enters a query using assistive technology method of choice into query entry box 1710. User can activate save AI query to Favorites icon 1705 to save the query. User can activate AI device icon 1706 to send a created alphanumeric query 1712 in query entry box 1710 to send directly to the AI device.

Figure 18:
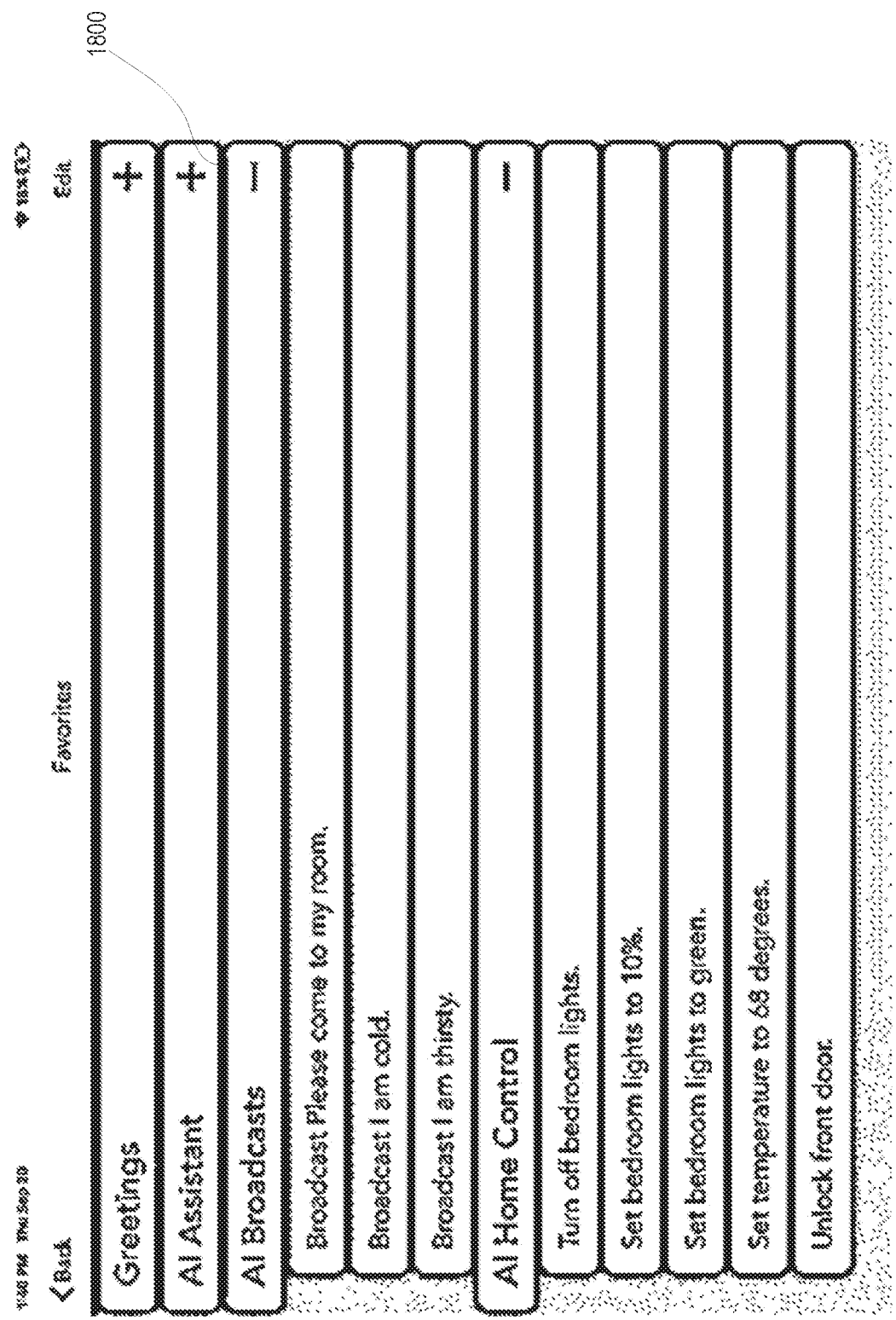
FIG. 18 is a screen depiction illustrating a favorites communication panel that is activated by user selection of favorites icon, according to one or more embodiments.

FIG. 18 is a favorites communication panel 1800 that is activated by user selection of access favorites icon 1704 (FIG. 17). In one or more embodiments, favorites communication panel 1800 can include automatically populated or user created control options such as an expandable list of greetings, an expandable list of selectable AI Assistants, an expanded list of AI broadcasts such as "Broadcast: Please come to my room"; "Broadcast: I am cold"; and "Broadcast: I am thirsty." An expanded list of AI Home Control affordances can include, for example, "Turn off bedroom lights", "Set bedroom lights to 10%; "Set bedroom lights to green"; "Set temperature to 68 degrees" and "Unlock front door". In one or more embodiments, AI Assistants facilitates queries that are related to audio, textual, environmental and home control responses/actions.

Figure 19:
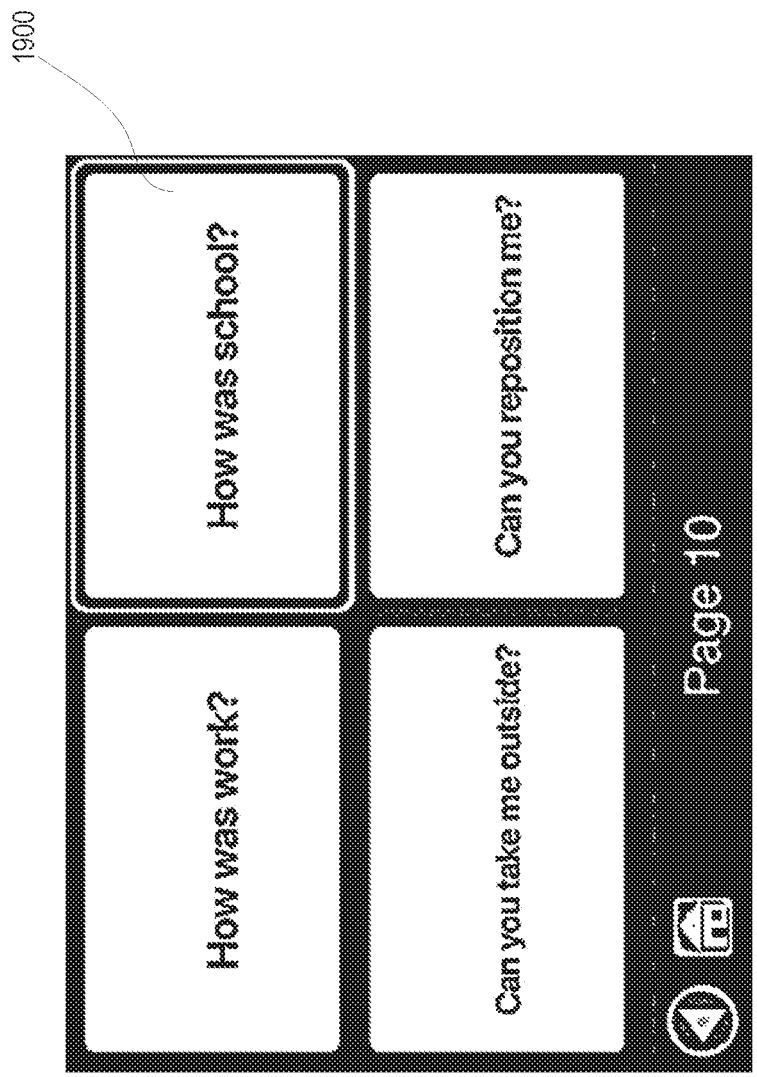
FIG. 19 is a screen depiction illustrating a context-driven user interface panel, according to one or more embodiments.

FIG. 19 is a screen depiction illustrating a context-driven user interface panel 1900. In a more advanced mode, the system gathers context about the user's environment and adjusts the communication options based on this context. Context for custom communication panels can be gathered through automatic queries to an AI device or through other sensor systems. Context could be time-of-day, persons in proximity of the user, temperature, day of the week, calendar entries, or any other input that would change what the user may want to say or do. A communication panel appears for the user on his computer (device) offering these customized choices. This could be in the form of a list or an array of buttons. A context generated button appears for "How was school", for example, if it is 4:00 pm on a weekday and the school-age daughter walks into the room. Context generated button "Can you take me outside?" appears, for example, if the caregiver is in the room in the afternoon and the current weather is sunny with no chance of rain.

In some examples, the NeuroNode system includes a prediction engine that predicts a subsequent query as a suggestion for the user, and provides the suggestion via the prediction box of the user interface layer. The prediction box may be a graphical user interface object that displays the suggestions provided by the prediction engine. It is noted that the prediction box is not necessarily displayed in the form of a square or rectangle, but can encompass any type of shape. The user may have executed one or two queries, and at this point in the process, the prediction engine may suggest a query or mapping as a suggestion to consider in the next query step via the prediction box, which is based on searches that other people have already done, searches that the same person has done, or certain mappings that other people have done in other contexts in order to not necessarily instruct the user on what to do, but rather as a reminder of a possibility to obtain more value out of the data of the data sources.

The prediction engine may check for previous data queries that map the query to predict a subsequent query. For example, the prediction engine may access the query history storing previously executed queries. The previously executed queries include the user's previous executed queries and other user's previous executed queries. Based on the query history, the prediction engine may determine whether any previous data queries match the query. If so, the prediction engine may determine one or more subsequent queries as suggestions for the user. For example, the previous data queries may indicate the next steps taken by the user or other users. As such, the prediction engine may predict one or more next steps for the user based on the previously executed queries of the query history, and provide these predictions in the prediction box of the user interface layer. As such, the NeuroNode system may lower the system's entry-barrier to the end-user by adapting to his/her previous usage, thereby allowing faster results to be provided by the business intelligence system. Furthermore, as indicated above, instead of restarting from scratch from every query, the NeuroNode system allows the user to build on each query, thereby building context.

In one or more embodiments, a server can be a key hub for communications with a variety of people, resources, assets, applications, and data sources that may have relevance to the user. As shown, the data sources may include a database of support network data (e.g., location, schedule, specialties, etc.) and a database of third-party app data and interfaces (e.g., social media, local search, navigation, etc.) and affinity programs. The data sources may also include data sources accessible over a network (e.g., local network, public network, private network, internet, IOT, etc.) such as a database of user data (e.g., medical, professional, public records, media, etc.), a database of local user data (e.g., police reports, trends, etc.) and a database of local data feeds (e.g., events, traffic, news, weather, camera feeds, etc.). Additional data sources may include user data sources including user data and analytics, including predictive analytics data, etc. The user data and analytics may include database(s) and engine(s), action/response engine, interface coordination database(s) and engine(s) assessment/prediction, learning database(s) and engine(s), (trending) context and behavior inference database(s) and engine(s), user profile, support network, schedule/calendar, devices/vehicles, user usage, hobbies, media posts, behavioral data, location/context profiles, historical location/context data, locations, places of interests (POIs) suppliers, user medical, personal data, and administration, security, and verification.

The server also serves as the primary analytical engine for developing and processing algorithms for profiling a user's behavior, tendencies, and probabilities for a wide range of possible situations, and for determining a variety of actions to, for, or on behalf of the user to improve the user's overall well-being. Such server functionality can be physically and/or logically configured in many forms. It can be centralized in one or more servers. It can be partitioned in a centralized manner such that functionality is split among different servers, such as one server being a communications network front-end for communicating with various users, devices, sensors, and other networks, while another server or set of servers does the analysis of the data. It can also be architected in distributed manner such that some or all of the functionality is performed on user and/or support network devices. It can be architected such that some or all of the functionality is done in the Cloud via various forms of cloud computing. Regardless of physical and/or logical distribution of functionality, it may be described as or referred to as a server unless otherwise indicated. The server serves as a monitoring, assessing, and controlling function of, for, and/or on behalf of the user. This could include providing a variety of alerts to various resources for the user.

Another aspect of exemplary embodiments of the present disclosure is the use of multiple location determination technologies or sources to determine locations of users and other persons/places/things. These technologies or sources include, but are not limited to, sensor networks (e.g., Internet of Things (IoT), etc.), GPS/Assisted GPS, cell tower identification, cell tower triangulation (TDOA, AFLT), beacons, Radio Frequency fingerprinting, Real-Time Location Services (RTLS), Wi-Fi based location systems, Radio Frequency Identification (RFID) based location systems and similar systems, drones, crowdsourcing, hybrids, simultaneous localization and mapping (SLAM), and/or combinations of these or other location determination systems. These location determination systems may be on, worn or carried by, used by, embedded in, or nearby the user.

Not all aspects of the present disclosure need to be centralized in the server. The user's local device(s) may also have functionality as disclosed herein, both for Peer-to-Peer, IoT, Mesh, ZigBee, LPWAN, Star, Client/Server, and/or machine-to-machine (M2M) networking, situations and in circumstances where the server or other parts of the present disclosure are not operating or accessible. An example of this functionality is in the device on/in/around the user detecting a high-risk situation and the user attempting to enter and drive a car in an underground garage (thereby preventing a GPS locate).

The user's device would automatically connect with the vehicle's transportation system (e.g., personal vehicle, friend or colleague's vehicle, transportation service like Uber, airlines, public transportations, etc.) to inform or provide an alert of a high-risk situation and proceeding to disable the car. Indeed, many, even all of the server's functions could conceivably be done in one or more of the user's device(s) or in other computing/data processing architectures such as cloud computing; a centralized server is a convenient/logical way to represent many of the present disclosure's functions, but not inherently necessary to its overall functionality.

Devices that can be associated with the user include but are not limited to portable devices such as mobile phones/smartphones, tablets, laptops, other portable or mobile devices, etc.; wearable devices and tags on or in clothing, jewelry, shoes, watches, etc.; mobile payment devices/wallets, etc.; embedded sensors, tags, chips or other electronics that can be implanted or ingested (e.g., ingestibles or implantables, etc.) in a user, augmented reality and heads-up displays (e.g. Google GLASS, etc.) and virtual reality-enabling systems. Fixed or mobile/fixed hybrid devices such as desktop computers and smart home connected devices that can also be associated with the identity and/or location user are also part of aspects of some exemplary embodiments of the present disclosure. For example, additional examples of smart home connected devices include a TV, refrigerator, and microwave. As more and more devices become smart, the smart device will have the ability to capture data that will help determine a person's location/context through onboard or connected data capture devices such as video, audio, and/or other sensors. Combined with the device's known location (or ability to determine the device's location), and the connectivity associated with communicating to and from these devices (also known as the Internet of Things or "IoT"), these devices/networks may provide new key sources of personal context information.

The IoT user-related sensors, devices, and networks may include smart vehicle, connected vehicle, driverless vehicle sensors, devices, and networks, such as cars, trucks, aircraft, trains, boats, RVs/rec vehicles, etc. The IoT user-related sensors, devices, and networks may include nearby human sensors, devices, and networks, such as nearby (to the user and/or support resource) person(s), devices, networks and sensors—including proximity and/or access to person(s) et al. and contextual data on, in or near that person as well as groups of persons and activities. The IoT user-related sensors, devices, and networks may include smart office, work environment sensors, devices, and networks, such as temperature, entry/exit, security, work-activity related, stress (mental or physical)-related, productivity-related, co-worker, office/work area-related. The IoT user-related sensors, devices, and networks may include smart city sensors, devices, and networks, such as public spaces and infrastructure with associated sensors, devices, and/or networks (e.g., that user/support resources, etc.) including parking, meters, advertising, police, first responders, etc.) that are in proximity of, connected to, and/or associated with that provide location/contextual information about user, support resources, and activities to help detect, anticipate, and manage situations. In various embodiments, a learning engine is provided that utilizes artificial intelligence and other learning algorithms and methods to learn from a user's behavior and to refine various systems, algorithms, and processes, such as a user's likelihood of relapse, effectiveness of actions taken, and types and frequency of data collected.

Numerous communication methods to/from the user and other resources are used in various embodiments of the present disclosure. These can include (but are not limited to) text/SMS/MMS, voice calls, email, social media, video, peer-to-peer and machine-to-machine communications, instant messaging, voice messaging/mail, 3rd party applications, heads-up displays (such as Google GLASS), hologram projections, and other applicable voice and data methods and mediums.

As discussed before, interfaces with third party applications may be provided in various embodiments. In various embodiments, a wide variety of interfaces may be provided to interact with the user, support network, and third parties. Such interfaces include but are not limited to: Direct manipulation interface (e.g. augmented/virtual reality), Graphical user interfaces, Web-based user interfaces, Touchscreens, Command line interfaces (e.g., command string input), Touch user interfaces, Hardware interfaces (e.g. knobs, buttons), Attentive user interfaces (e.g., that determine when to interrupt a person), Batch interfaces, Conversational interfaces, Conversational interface agents (e.g. animated person, robot, dancing paper clip), Crossing-based interfaces (e.g., crossing boundaries versus pointing), Gesture interfaces (e.g. hand gestures, etc.), Holographic user interfaces, Intelligent user interfaces (e.g., human to machine and vice versa), Motion tracking interfaces, Multiscreen interfaces, Non-command user interfaces (e.g., infer user attention), Object-oriented user interfaces (e.g., to manipulate simulated objects), Reflexive user interfaces (e.g., achieves system changes), Search interface, Tangible user interfaces (e.g., touch), Task-focused interfaces (e.g., focused on tasks, not files), Text-based user interfaces, Voice user interfaces, Natural-language interfaces. Zero-input (e.g., sensor-based) interfaces, Zooming (e.g., varying-levels of scale) user interfaces. Various mechanisms may be provided for selecting/modifying the interfaces based on the user's context. In various embodiments, robots and robotics may be used. In various embodiments, scheduling and to-do lists of the user are utilized, as well as the user's support network.

In some embodiments, the two-way communication system may be integrated with third-party providers, such as Amazon ALEXA and Apple SIRI, such that a request from other mobile devices may be received.

In one or more embodiments, the present disclosure relates to a patient monitor with a help screen system to monitor a user's health status. A patient monitor, such as a pulse oximeter, is provided that displays physiological information and includes a user-input device that allows a user to access an input screen system. The system may be integral to the patient monitor or in a separate device. In operation, the healthcare provider may access this system to seek answers for questions about the patient. In one or more embodiments, the present techniques also apply to providing information regarding system or patient warnings or alarms, patient monitoring data or reports, and so on.

In one or more embodiments, a monitoring system (e.g., pulse oximeter) may include a patient monitor configured to display physiological information related to a patient. The monitoring system may include a user input device in communication with the monitor. The user input device may cause the monitor to display, for example, a report of patient data, a report of performance of the patient monitor, a warning, an alarm, a help message, or any combination thereof, and so on. The information displayed may be context sensitive to the current status of the patient monitor or to a current point in a menu tree of a control scheme of the patient monitor, for example.

The approaches described herein provide users with a way to view and organize content by providing a classic hierarchical visualization structure in various computing environments, for example desktop and mobile environments. In some approaches, the user may rearrange the navigation hierarchy based on the provided content, further enhancing the context-sensitive nature of the navigation.

In one or more embodiments, a display apparatus is provided having an interface with an input and an output and a processor coupled to the interface. The output is configured to display a first panel at a variable panel display portion of a display. The first panel includes one or more first selectable nodes associated with a control system and information associated with the control system.

Upon the input receiving a selection of one or more of the selectable nodes, the processor is configured to access a server and present a panel associated with the selected node at the variable panel display portion. This panel includes one or more second selectable nodes and information associated with the selected node. The processor is further configured to adjust the size of the variable panel display portion displayed at the output to accommodate a number of panels and to allow navigation between the panels that is independent of information displayed at a working portion of the display. In some examples, the processor is further configured to present the first panel and the panel associated with the selected node adjacent to each other on the variable display portion via the output.

In one or more embodiments, the display apparatus may further include any number of additional panels which are configured to display the selected node and information associated therewith. The processor may be configured to determine the size of the variable panel display portion corresponding to a maximum number of displayable panels in the variable panel display portion and compare the determined size to the number of presented panels and thereafter display the maximum number of displayable panels in the variable panel display portion.

Approaches are provided that allow for efficiently visualizing hierarchical data structures across a number of different devices having displays. In one aspect, the approaches allow for the resizing of the hierarchical structure to accommodate displays having a number of different configurations. The hierarchical structure may also be navigated while a working portion of the display maintains the content contained therein via a graphical user interface (or in some instances, an audio cue). The hierarchical structure may provide an indication for the current visible panels and may be navigable to allow the display of alternative panels. The hierarchical structure may also include contextual information (such as, for example, a folder name, title, or other common identifier) beyond identification information.

The principles of user interface and user signaling disclosed in this document are applicable for use with information from any sensors that can provide information related to motion and/or position of body parts and/or physiological states or any other objects that can provide an indication of motion of users' body parts. Further, this motion/position information can be derived using a variety of sensors including but not restricted to accelerometers, gyroscopes, image sensors, wave field sensors, radars, electric field sensors, acoustic sensors, ultrasonic sensors, EMG sensors, OCG sensors, resistive sensors, as well as others. Further, some user actions may not be detectable visibly from outside but be detectable by other sensors. For example, users can change their meditation or attention level consciously. Alternatively, they can also intentionally change the level of their Alpha, Beta, Theta or Delta brain waves. These levels and/or level changes can be measured by brainwave, EEG or other suitable sensors.

The term Primary Control Expression (PCE) is used to refer to user actions that can be used to signify user intention. This application also introduces the concept of Primary Control Motion (PCM) which is analogous to PCE and therefore can be used to signify user intention. The concept of Primary Control Motion (PCM) is similar to the concept of PCE. While a PCE is facial expression, a PCM can be a designated bodily motion or pose/position/orientation (of a designated set of one or more body parts) PCM can include designated combination(s) or sequence(s) of bodily motions that can include motions of the entire head, eyeballs, hands, fingers, arms, shoulders, torso, legs, feet, toes, etc Note that motions of the entire head such as head nods, head tilts, side to side heads motions or head rolls, etc. are considered to be head/body motions and not facial expressions. Motion of the eyeballs is also considered to be body motion and not a facial expression. However, motion of eyelids such as opening/closing of eyes, blinking and winking are considered to be facial expressions. Similarly, motion of eyebrows such as eyebrow raises, furrowing of eyebrows and other eyebrow motions are considered to be facial expressions. Just as PCEs, PCMs are accorded special significance when communicating with electronic devices. A PCM or a PCE can be used as an enabler, trigger, modifier, or even as a specific command, while communicating with an Electronic Device. PCE and PCM can also comprise actions such as entering meditative/attentive states, tensing internal muscles, relaxing, deep breathing, etc, as these actions can be used to signify user intention and thereby can be used in heuristics explained just as any other body actions. PCEs and PCMs together can be called as User Intention actions.

Neurosky, Inc. (http://neurosky.com) is one vendor that provides hardware and software to measure brainwaves and detect changes in meditation and attention level of the user. Some embodiment then can use brainwave sensors that provide readings of either meditation level or attention level or any other biometric quantity that the user can consciously have an effect on and/or can cause a change in magnitude, frequency, direction or other measurable attribute. For example, instead of performing a facial expression, the user can increase or decrease meditation or attention level, which then can be treated as "PCE" information and used in the heuristics/principles as described in this and above referenced documents. Brainwave sensors, EEG and other biometric sensors can be used as PCE sensors and used to control electronic devices. Similarly, certain conscious bodily muscular action may be hard to detect visibly, however, may be easily detectable by EMG sensors and other sensors. For example, clenching of the teeth or different parts of lower jaw, tensing throat, other parts of face or head, scalp, various auricularis muscles, parts of torso, shoulders, arms, legs, feet, fingers, toes, thighs, calves, or various sphincters of the body may not be externally visible but could be detected by EMG or other sensors. Again, these sensors can be used as PCE/PCM sensors and all the heuristics defined for PCE/PCM sensors can be used with these sensors as well.

All of the above disclosed concepts/principles/heuristics/techniques/algorithms, etc. can be used in variety of different fields and applications. Some of the examples are Augmentative and alternative communication (AAC), Assistive Technology, Speech Generation Devices, Augmented/Mixed/Virtual Reality, Desktop & Mobile Computing, Gaming, Industrial Control, Healthcare, Defense, Aviation, Transportation, Manufacturing, Product Lifecycle Management, Aerospace, & others. All the concepts/principles/heuristics/techniques/algorithms, etc. disclosed in this document can also be used with all the apparatuses/devices disclosed in the referenced documents, as well as with devices including but not limited to head worn devices such as smart glasses, smart helmets, virtual/mixed/augmented reality devices, head worn controllers, in-ear controllers, head phones, ear plugs, head bands and neck bands. Further, they are also applicable to other body worn devices such arm/wrist bands, devices utilizing wearable sensors and smart watches, devices embedded inside the user's body, as well as devices that are not physically worn in/on user's body such as smart phones, tablets, desktop computers, smart TVs, set top devices, and others that may possibly utilize image, radar, sonar, sound/voice, ultrasonic, laser and other sensors to sense any or all body action and/or physiological states.

Persons knowledgeable in the art can see that the above disclosed concepts/principles/heuristics/techniques/algorithms, etc., including but not limited to combinations of different types of motions and signals may occur simultaneously or in tandem. Further, motions can be substituted by other bodily and/or mental actions performed by the user in the use/application of the disclosed concepts/principles/heuristics/techniques/algorithms, etc. Some or all of the above disclosures can be used to define or implement computer implementable methods or processes, to design and create part of user interfaces to electronic devices, to devise/create software modules/applications/programs, API, to manufacture non-transient storage media that can contain computer executable instructions based on some or all of the teachings of the disclosures, and/or to manufacture devices or apparatuses that implement some or all of the teachings of the disclosures.

While the disclosure has been described with reference to exemplary embodiments, it will be understood by those skilled in the art that various changes may be made and equivalents may be substituted for elements thereof without departing from the scope of the disclosure. In addition, many modifications may be made to adapt a particular system, device or component thereof to the teachings of the disclosure without departing from the essential scope thereof. Therefore, it is intended that the disclosure not be limited to the particular embodiments disclosed for carrying out this disclosure, but that the disclosure will include all embodiments falling within the scope of the appended claims. Moreover, the use of the terms first, second, etc. do not denote any order or importance, but rather the terms first, second, etc. are used to distinguish one element from another.

The terminology used herein is for the purpose of describing particular embodiments only and is not intended to be limiting of the disclosure. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The description of the present disclosure has been presented for purposes of illustration and description but is not intended to be exhaustive or limited to the disclosure in the form disclosed. Many modifications and variations will be apparent to those of ordinary skill in the art without departing from the scope of the disclosure. The described embodiments were chosen and described in order to best explain the principles of the disclosure and the practical application, and to enable others of ordinary skill in the art to understand the disclosure for various embodiments with various modifications as are suited to the particular use contemplated.

What is claimed is:

1. A method comprising:
   receiving a bioelectrical signal from a set of bioelectrical sensors by an electronic processor of an electrode switch device;
   automatically adjusting, by the electronic processor, a switch range with initial values of a resting threshold and a switch threshold;
   monitoring, by the electronic processor, a range of two or more instances of a bioelectric signal from a set of electrodes placed on a user at a target muscle site, each instance comprising a first resting level, followed by a switching level that is greater than the first resting level, and second resting level that is less than the switching level;
   comparing, by the electronic processor, an amplitude of the bioelectric signal to the switch range that is defined between the resting threshold and the switch threshold that is greater than the resting threshold;
   detecting, by the electronic processor, a trend in the amplitude across the two more instances of the biometric signal;
   automatically adjusting, by the electronic processor, the switch range based at least in part on the trend in the amplitude of the bioelectric signal based on a change in at least one of: (i) fatigue level of the user; and (ii) electrode interface condition to respond reliably and accurately to minimal signals at the target muscle site that are volitionally generated by a user;
   determining, by the electronic processor, that the amplitude of the bioelectrical signal has changed from less than the switch range to greater than the switch range; and
   in response to determining that the amplitude of the bioelectrical signal has changed from less than the switch range to greater than the switch range, transmitting, by the electrode switch device, a switch signal to control a user interface device.

2. The method of claim 1, further comprising:
determining, by the electronic processor of the electrode switch device, a context of the user;
automatically selecting, by the electronic processor of the electrode switch device, a control affordance of more than one control affordance that is associated with the context of the user to provide context sensitive switching that anticipates what the user wants to say or do and without requiring user input to manually designate one of the more than one control affordance to interact with; and
presenting the control affordance on the user interface device to solicit a volitional response by the user.

3. The method of claim 2, wherein:
determining, by the electronic processor of the electrode switch device, the context of the user comprises determining an ambient environmental condition based on an ambient environment sensor proximate to the user; and
the user interface device comprises an environmental control interface.

4. A system comprising:
a set of bioelectrical electrodes configured to attach to a user; and
an electrode switch device containing an electronic processor that is in communication with the set of bioelectrical sensors to receive a bioelectrical signal and that projects functionality to:
automatically adjust a switch range with initial values of a resting threshold and a switch threshold;
monitor a range of two or more instances of the bioelectrical signal from the set of bioelectrical electrodes, each instance comprising a first resting level, followed by a switching level that is greater than the first resting level, and second resting level that is less than the switching level;
comparing an amplitude of the bioelectric signal to the switch range that is defined between the resting threshold and the switch threshold that is greater than the resting threshold;
detect a trend in the amplitude across the two more instances of the biometric signal;
automatically adjust the switch range based at least in part on the trend in the amplitude of the bioelectric signal based on a change in at least one of: (i) fatigue level of the user; and (ii) electrode interface condition to respond reliably and accurately to minimal signals at the target muscle site that are volitionally generated by a user;
determine that the amplitude of the bioelectrical signal has changed from less than the switch range to greater than the switch range; and
in response to determining that the amplitude of the bioelectrical signal has changed from less than the switch range to greater than the switch range, transmit a switch signal to control a user interface device.

5. The system of claim 4, further comprising monitoring, by the processor, a movement sensor that is configured to attach to the user, wherein controlling the device with the switch signal is further in response to determining that a movement signal sensed by the movement sensor concurrently with the bioelectrical signal is less than a spasm threshold.

6. A system comprising:
a set of bioelectrical electrodes configured to attach to a user;
a user interface device; and
an electrode switch device containing an electronic processor that is in communication with: (i) the set of bioelectrical sensors to receive a bioelectrical signal; and (ii) the user interface device and that projects functionality to:
determine, by the processor, a context of the user;
automatically select the control affordance of more than one control affordance that is associated with the context of the user to provide context sensitive switching that anticipates what the user wants to say or do;
automatically adjust a switch range with initial values of a resting threshold and a switch threshold;
monitor a range of two or more instances of the bioelectrical signal from the set of bioelectrical electrodes, each instance comprising a first resting level, followed by a switching level that is greater than the first resting level, and second resting level that is less than the switching level;
compare an amplitude of the bioelectric signal to the switch range that is defined between the resting threshold and the switch threshold that is greater than the resting threshold;
detect a trend in the amplitude across the two more instances of the biometric signal;
automatically adjust the switch range based at least in part on the trend in the amplitude of the bioelectric signal based on a change in at least one of: (i) fatigue level of the user; and (ii) electrode interface condition to respond reliably and accurately to minimal signals at the target muscle site that are volitionally generated by a user;
determine that the amplitude of the bioelectrical signal has changed from less than the switch range to greater than the switch range; and
in response to determining that the amplitude of the bioelectrical signal has changed from less than the switch range to greater than the switch range, transmit a switch signal to control the user interface device associated with the control affordance.

7. The system of claim 6, further comprising an ambient environment sensor proximate to the user; wherein:
the processor determines the context of the user by determining an ambient environmental condition based on the ambient environment sensor; and
the user interface comprises an environmental control interface.

8. The method of claim 1, further comprising: disallowing, by the electronic processor of the electrode switch device, any additional switch signals after the switch signal until the amplitude of the bioelectrical signal is less than a signal off threshold.

9. The method of claim 3, wherein determining the context of the user comprises determining a location of the user by the electronic processor of the electrode switch device.

10. The method of claim 3, wherein determining the ambient environmental condition comprises determining a temperature by the electronic processor of the electrode switch device.

11. The method of claim 1, further comprising:
presenting more than one control affordance on the user interface device;
monitoring at least one eye of the user via an eye-tracking camera;
recognizing, via the eye-tracking camera, a gaze target of one of the more than one control affordance; and in response to determining, by the electronic processor of the electrode switch device, that the amplitude of the bioelectrical signal has changed from less than the switch range to greater than the switch range while maintaining the gaze target, displaying, via the user interface device a user selection.

12. The system of claim 4, further comprising an eye-tracking camera and the user interface device, wherein the processor is communicatively coupled to the eye-tracking camera and the user interface device and projects further functionality to:
   present more than one control affordance on the user interface device;
   monitor at least one eye of the user via an eye-tracking camera;
   recognize, via the eye-tracking camera, a gaze target of one of the more than one control affordance; and
   in response to determining that the amplitude of the bioelectrical signal has changed from less than the switch range to greater than the switch range while maintaining the gaze target display, via the user interface device, a user selection.

13. The system of claim 4, wherein the processor disallows any additional switch signals after the switch signal until the amplitude of the bioelectrical signal is less than a signal off threshold.

14. The system of claim 7, wherein the processor determines the context of the user by determining a location of the user.

15. The system of claim 7, wherein the processor determines the ambient environmental condition by determining a temperature.

16. The method of claim 1, wherein the electrode switch device consists essentially of a standalone electromyography (EMG) switch having a housing configured to be wearable by the user and containing the electronic processor powered by a battery and that receives the bioelectrical signal from the set of bioelectrical sensors physically connected to the EMG switch by one: (i) an attachment to the housing; and (ii) attachment via respective electrical wires to the housing, the electronic processor communicatively coupled to the user interface device that is external to the housing.

17. The system of claim 4, wherein the electrode switch device consists essentially of a standalone electromyography (EMG) switch having a housing configured to be wearable by the user and containing the electronic processor powered by a battery and that receives the bioelectrical signal from the set of bioelectrical sensors physically connected to the EMG switch by one: (i) an attachment to the housing; and (ii) attachment via respective electrical wires to the housing, the electronic processor communicatively coupled to the user interface device that is external to the housing.

18. The system of claim 6, wherein the electrode switch device consists essentially of a standalone electromyography (EMG) switch having a housing configured to be wearable by the user and containing the electronic processor powered by a battery and that receives the bioelectrical signal from the set of bioelectrical sensors physically connected to the EMG switch by one: (i) an attachment to the housing; and (ii) attachment via respective electrical wires to the housing, the electronic processor communicatively coupled to the user interface device that is external to the housing.

\* \* \* \* \*